United States Patent
Hu et al.

(10) Patent No.: US 12,083,512 B2
(45) Date of Patent: Sep. 10, 2024

(54) MICROFLUIDIC ANALYSIS OF LIGAND INDUCED CELL EXPRESSION

(71) Applicant: European Molecular Biology Laboratory, Heidelberg (DE)

(72) Inventors: Hongxing Hu, Heidelberg (DE); Samantha Seah, Heidelberg (DE); Christoph A. Merten, Heidelberg (DE)

(73) Assignee: EUROPEAN MOLECULAR BIOLOGY LABORATORY (DE)

( * ) Notice: Subject to any disclaimer, the term of this patent is extended or adjusted under 35 U.S.C. 154(b) by 0 days.

(21) Appl. No.: 16/069,824

(22) PCT Filed: Jan. 13, 2017

(86) PCT No.: PCT/EP2017/050620
§ 371 (c)(1),
(2) Date: Jul. 12, 2018

(87) PCT Pub. No.: WO2017/121832
PCT Pub. Date: Jul. 20, 2017

(65) Prior Publication Data
US 2019/0022645 A1    Jan. 24, 2019

(30) Foreign Application Priority Data
Jan. 14, 2016  (EP) .................... 16151298

(51) Int. Cl.
*B01L 3/00*   (2006.01)
*C07K 16/28*  (2006.01)
(Continued)

(52) U.S. Cl.
CPC ............. *B01L 3/502715* (2013.01); *B01L 3/502761* (2013.01); *C07K 16/28* (2013.01);
(Continued)

(58) Field of Classification Search
CPC ......... B01L 3/502715; B01L 3/502761; B01L 2200/0647; B01L 2300/021; C07K 16/28;
(Continued)

(56) References Cited

U.S. PATENT DOCUMENTS

2016/0252495 A1* 9/2016 Ricicova ............. B01L 3/50273
 506/9
2018/0030515 A1* 2/2018 Regev ................. C12N 15/1096

FOREIGN PATENT DOCUMENTS

WO   2009/158024    12/2009
WO   2013/036997    3/2013

OTHER PUBLICATIONS

Macosko et al. (Cell, 161, p. 1202-1214, 2015).*
Dura et al. (Nat. Commun. 2015, 6:5940, 13 pages).*
Guo et al. "Droplet microfluidics for high-throughput biological assays", Lab on a Chip, 2012, 12, pp. 2146-2155.
El Debs et al., "Functional Single-cell Hybridoma screening using droplet-based microfluidics", Proceedings of the National Academy of Sciences of the United States of America, vol. 109, No. 29, Jul. 17, 2012, pp. 11570-11575.
(Continued)

*Primary Examiner* — Jeremy C Flinders
(74) *Attorney, Agent, or Firm* — Merchant & Gould P.C.

(57) ABSTRACT

The present invention relates to the field of microfluidics and in particular to analysing the gene expression of a cell in response to a ligand expressed in the same microfluidic compartment. By barcoding the transcriptome of the cell and of the expression system generating the ligand, the effect of the ligand on the cell expression can be discerned. The invention provides microfluidic compartments and methods for this purpose.

26 Claims, 5 Drawing Sheets

(51) Int. Cl.
   *C12Q 1/6806* (2018.01)
   *C12Q 1/6844* (2018.01)
   *C12Q 1/686* (2018.01)
   *C40B 20/08* (2006.01)

(52) U.S. Cl.
   CPC ......... *C12Q 1/6806* (2013.01); *C12Q 1/6846* (2013.01); *C12Q 1/686* (2013.01); *B01L 2200/0647* (2013.01); *B01L 2300/021* (2013.01); *C12Q 2600/158* (2013.01); *C12Q 2600/16* (2013.01); *C12Q 2600/166* (2013.01); *C40B 20/08* (2013.01)

(58) Field of Classification Search
   CPC ................ C12Q 1/6806; C12Q 1/6846; C12Q 2600/158; C12Q 2600/16; C12Q 2600/166; C12Q 1/686; C40B 20/08
   See application file for complete search history.

(56) References Cited

OTHER PUBLICATIONS

International Search Report and Written Opinion, International Patent Application No. PCT/EP2017/050620, Apr. 6, 2017 (15 pages).
Shields et al., "Magnetographic array for the capture and enumeration of single cells and cell pairs", Biomicrofluidics 8, 041101, XP55669585A, Jul. 1, 2014 (5 pages).
Office Action, European Patent Application No. 17701645.8, Feb. 24, 2020 (5 pages).
Machine translation of Office Action issued in Chinese Patent Application No. 201780015864.2, Apr. 12, 2021 (12 pages).
Shan Gao, The R Programming Language and Bioconductor Bioinformatics Application, Tianjin Science and Technology Translation Publishing Co., Ltd., Jan. 2014, p. 159; Cited in Chinese Patent Application No. 201780015864.2.

\* cited by examiner

MICROFLUIDIC ANALYSIS OF LIGAND INDUCED CELL EXPRESSION

FIELD OF THE INVENTION

The present invention relates to the field of microfluidics and in particular to analyzing the gene expression of a cell in response to a ligand expressed in the same microfluidic compartment. By barcoding the transcriptome of the cell and of the expression system generating the ligand, the effect of the ligand on the cell expression can be discerned. The invention provides microfluidic compartments and methods for this purpose.

BACKGROUND OF THE INVENTION

Figure 1:
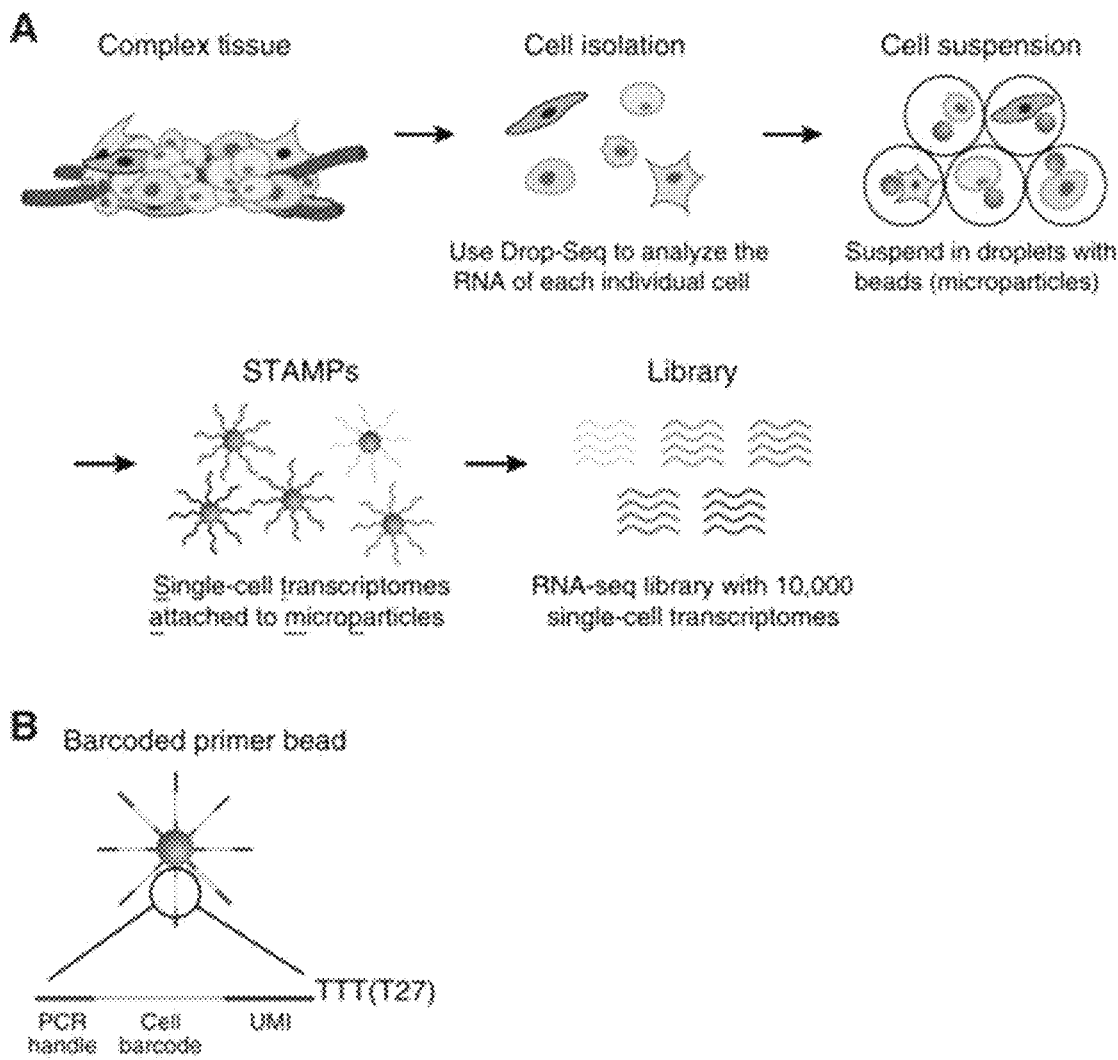

Compartment based microfluidics, such as droplet based microfluidics, holds great potential for high throughput screening applications. The encapsulation of single cells into compartments allows screening of cell products such as antibodies at very high throughput, e.g. up to several hundred thousand samples per day. Single cell RNA sequencing, also termed RNAseq, has gained a lot of scientific and commercial attention. Its goal is the analysis of global gene expression patterns on the single-cell level, thus allowing to analyse and reveal distinct cell types in heterogeneous populations such as stem cells, tumours or developing embryos. Fluidigm Corp. has become the market leader of this technology offering valve-based microfluidic solutions for single cell RNAseq. Their C1 system can process up to 96 cells in a single run and the next generation of this platform will have a throughput of up to 800 cells in one go. In parallel, nanowells (Fan, H. C., G. K. Fu, and S. P. A. Fodor, Science, 2015. 347(6222): p. 628) and droplet based microfluidic technology (Macosko, E. Z. et al., Cell, 2015. 161(5): p. 1202-14; Klein, A. M., et al., Cell, 2015. 161(5): p. 1187-201; Rotem, A., et al., Nat Biotechnol, 2015. 33(11): p. 1165-72) have been developed, enabling the processing of up to 10,000 cells for RNAseq or ChIPseq. In these systems, single-cells are encapsulated into microfluidic droplets or nanowells, together with single beads displaying polyT nucleotides with unique barcodes (FIG. 1). After encapsulation the cells are lysed and all cellular mRNAs hybridize with the barcoded polyT primers, thus ensuring a physical linkage with the barcode. Either at this stage or after performing an additional reverse transcription step within the droplets all samples can be pooled and applied to next generation sequencing. Due to the barcoding the expression patterns of individual cells can still be distinguished, thus revealing differences within the population. Prior art single cell sequencing techniques and studies focus exclusively on characterizing single cells individually. They do not, however, aim at co-encapsulating two different cells and sequencing their transcriptomes at the same time. Such a co-encapsulation of two different cell types into the same droplet and labeling the mRNAs of both cell types with the same barcodes has huge biomedical potential: It allows analyzing cell-cell interactions, e.g. how cell A reacts to the presence of cell B or factors secreted by cell B, and could in particular be exploited for screening genetically-encoded drug candidates such as monoclonal antibodies, which have annual sales of more than 50 billion US$, in a highly multiplexed fashion.

To do so, the inventor implemented a novel screening approach, which allows for the analysis of cell expression in response to unknown ligands expressed by a cell, wherein hundreds of different unknown ligands can be tested for an effect on cell expression, and wherein the identity of the ligands can be determined and linked to a cell and its gene expression, all at the same time. For example, as a starting point one can immunize animals with human cancer cells or membrane extracts thereof. Subsequently, plasma cells secreting antibodies against hundreds or even thousands of known or so far uncharacterized cell epitopes and receptors can be isolated and applied to screens based on the co-compartmentalization of a single plasma cell and a single cancer cell into compartments, together with a single bead displaying polyT primers harboring unique barcodes (a different barcode for each bead and hence for each compartment). This is fundamentally different to previous uses of single cell RNAseq, aiming for the specific encapsulation of only a single cell and considering the co-compartmentalization of more than one cell into a compartment as an undesired accident. Subsequent to the generation of compartments hosting plasma and cancer cells, the samples can be incubated to allow for efficient secretion of antibodies acting on the target cell. It is well known that antibodies cannot only bind to surface receptors, but as well trigger signal cascades ultimately resulting in changed expression profiles (Silva, H. M., et al., Immunol Lett, 2009. 125(2): p. 129-36; Franke, A., et al., PLoS One, 2011. 6(2): p. e16596). After an incubation period, the plasma cell and the cancer cell can be lysed inside the compartments, and the cellular mRNAs hybridize with the barcoded polyT primer in the compartments. This ensures that the mRNAs of both cell types in each compartment is physically linked to/labeled with the same barcode. In other words, both the antibody encoding genes of the animal plasma cell as well as the genes expressed in the human cancer cell upon contact with the animal antibodies get labeled with the same barcode. Either at this step or after first strand cDNA synthesis inside the compartments, the contents of all compartments are pooled. Subsequently a next generation sequencing library is generated and sequenced. Then, the resulting data is analyzed based on the barcodes revealing both the identity of the antibody that was present in a particular compartment as well as its effect on the expression pattern of the human cell. This allows to specifically look for antibodies with a desired functional effect, as can be derived from the expression pattern, e.g. activation/inactivation of particular pathways. This approach enables the screening of millions of antibodies for hundreds or even thousands of effects in parallel, based on the immunization of the animal with entire cells or membrane extracts, including hundreds or thousands of epitopes. This level of multiplexing has so far not been achieved in drug discovery and is provided by the present invention.

SUMMARY OF THE INVENTION

In a first aspect, the present invention relates to a plurality of microfluidic compartments, wherein at least 1% of said compartments form a subset in which each compartment comprises
  (i) a first cell,
  (ii) one second cell or one cell-free expression system expressing a polypeptide ligand which is intended to specifically bind to a molecule or part thereof accessible on the surface of the first cell,
  (iii) a set of barcode oligonucleotides each comprising a barcode sequence unique to the set and a sequence capable of binding specifically to mRNA and/or cDNA.

In a second aspect, the present invention relates to a method for generating a plurality of microfluidic compartments according to the first aspect, comprising the steps of:
(a) introducing into a microfluidic system: (i) a fluid comprising a plurality of first cells, (ii) a fluid comprising a plurality of second cells or cell-free expression systems each expressing a polypeptide ligand which is intended to specifically bind to a molecule or part thereof accessible on the surface of a first cell, and (iii) a fluid comprising sets of barcode oligonucleotides, wherein the barcode oligonucleotides of each set comprises a barcode sequence unique to the set, and a sequence capable of binding specifically to mRNA and/or cDNA,
(b) repeatedly co-compartmentalizing a first cell, a second cell or cell-free expression system, and a set of barcode oligonucleotides into microfluidic compartments, such that the size of the subset of compartments in the plurality of compartments is at least 1%.

In a third aspect, the present invention relates to a method for determining the gene expression of a cell, comprising the steps:
(a) providing a plurality of microfluidic compartments according to the first aspect,
(b) lysing the cells comprised in the compartments,
(c) reverse transcribing mRNA released from the cells to cDNA,
(d) amplifying the cDNA,
(e) determining the sequence and optionally the respective amount of the cDNA, and
(f) selecting sequences comprising the same barcode sequence, wherein the following sequences are excluded:
sequences derived from a second cell or a cell-free expression system,
sequences comprising a unique barcode sequence that is not associated in other sequences with a nucleotide sequence encoding for a polypeptide ligand expressed by a second cell or a cell-free expression system,
sequences comprising a unique barcode sequence that is associated with a nucleotide sequence encoding for more than one polypeptide ligand expressed by a second cell or a cell-free expression system,
wherein step (c) or step (d) is carried out with a barcode oligonucleotides as a primer. Preferably, the method further comprises a step (g) of determining which polypeptide ligand was comprised in the same compartment as the cell from which the sequences selected in step (f) are derived from, comprising identifying, from the excluded sequences derived from a second cell or a cell-free expression system, the nucleic sequence encoding for a polypeptide ligand which is associated with the barcode sequence of the selected sequences of step (f).

In a fourth aspect, the present invention relates to the use of the method of the third aspect to determine (i) the effect of antibodies on the gene expression of a target cell, wherein the antibodies were raised by immunizing a vertebrate with said target cell or one or more molecules or parts therefrom accessible on its surface, or (ii) the effect of polypeptide ligands on the gene expression of a target cell, wherein the polypeptide ligand is derived from a library.

LEGENDS TO THE FIGURES

FIG. 1: Conventional Molecular Barcoding of Cellular Transcriptomes in Droplets (as described in Macosko, E. Z., et al., Cell, 2015. 161(5): p. 1202-14) A) Drop-Seq barcoding schematic. A complex tissue is dissociated into individual cells, which are then encapsulated in droplets together with microparticles (gray circles) that deliver barcoded primers. Each cell is lysed within a droplet; its mRNAs bind to the primers on its companion microparticle. The mRNAs are reverse-transcribed into cDNAs, generating a set of beads called "single-cell transcriptomes attached to microparticles" (STAMPs). The barcoded STAMPs can then be amplified in pools for high-throughput mRNA-seq to analyze any desired number of individual cells. B) Sequence of primers on the microparticle. The primers on all beads contain a common sequence ("PCR handle") to enable PCR amplification after STAMP formation. Each microparticle contains more than $10^8$ individual primers that share the same "cell barcode" (C) but have different unique molecular identifiers (UMIs), enabling mRNA transcripts to be digitally counted (D). A 30-bp oligo dT sequence is present at the end of all primer sequences for capture of mRNAs.

Figure 2:
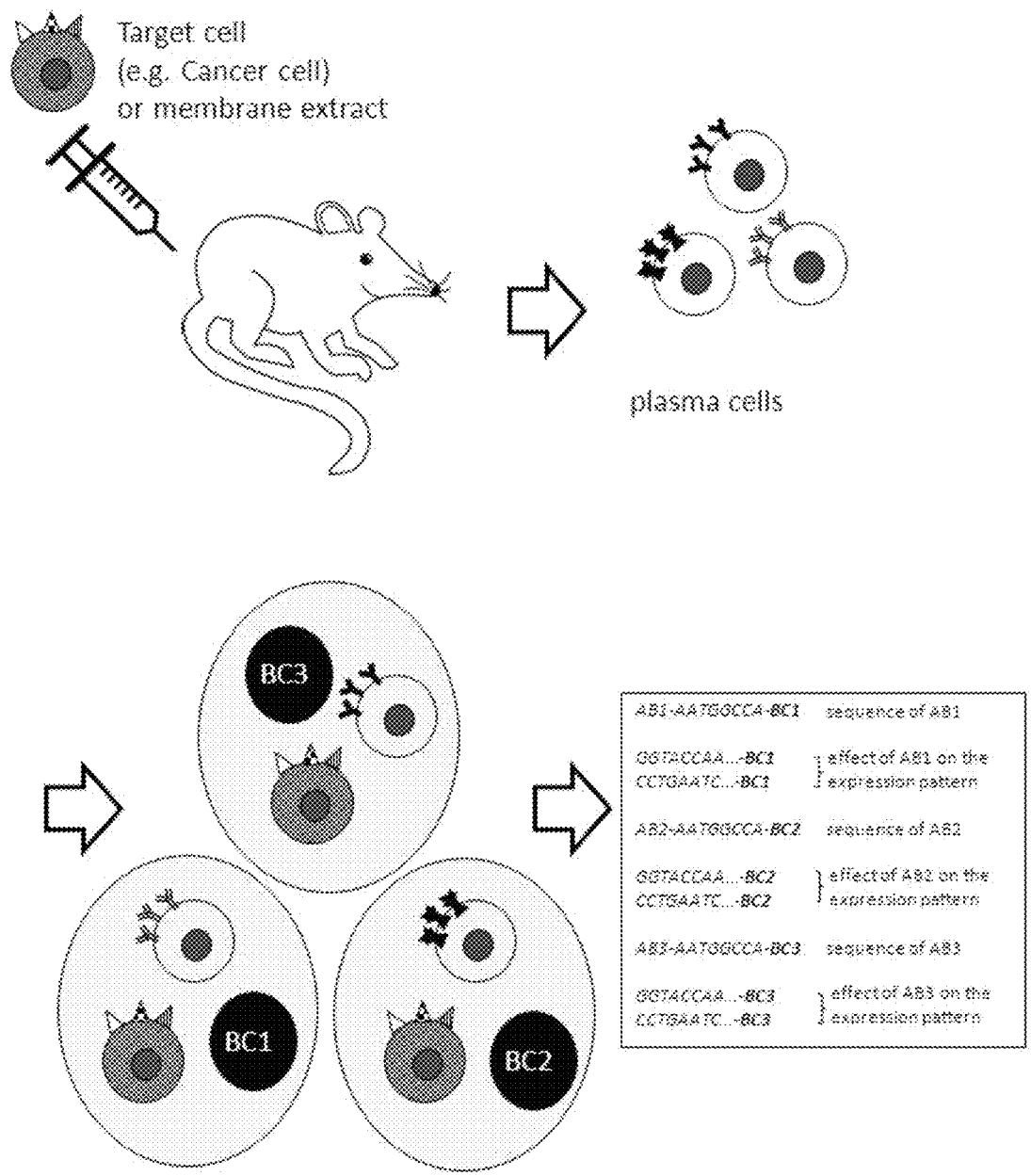

FIG. 2: Schematic of the novel approach for gene expression-based antibody screening. Animals are immunized with human cells or membrane extracts thereof. In consequence, the immunized animals will generate plasma cells expressing antibodies against hundreds or thousands of surface epitopes. These cells are isolated and encapsulated into microfluidic droplets on the single cell level, together with the human cell type used for immunization and barcoded polyT primers on beads (a different barcode for each bead and hence each droplet). Subsequently the droplets are incubated allowing the secreted antibodies to have an effect on the target cell's global gene expression pattern. As the next step, both cell types within the droplet are lysed and their mRNAs are labelled with the oligonucleotide barcode present on the bead (unique for each droplet and hence each plasma cell-target cell pair). Then next generation sequencing (RNAseq) is performed and the data is analyzed. In consequence, the effect of each antibody on cellular signaling can be determined, revealing many new therapeutic antibodies in a highly multiplexed fashion.

Figure 3:
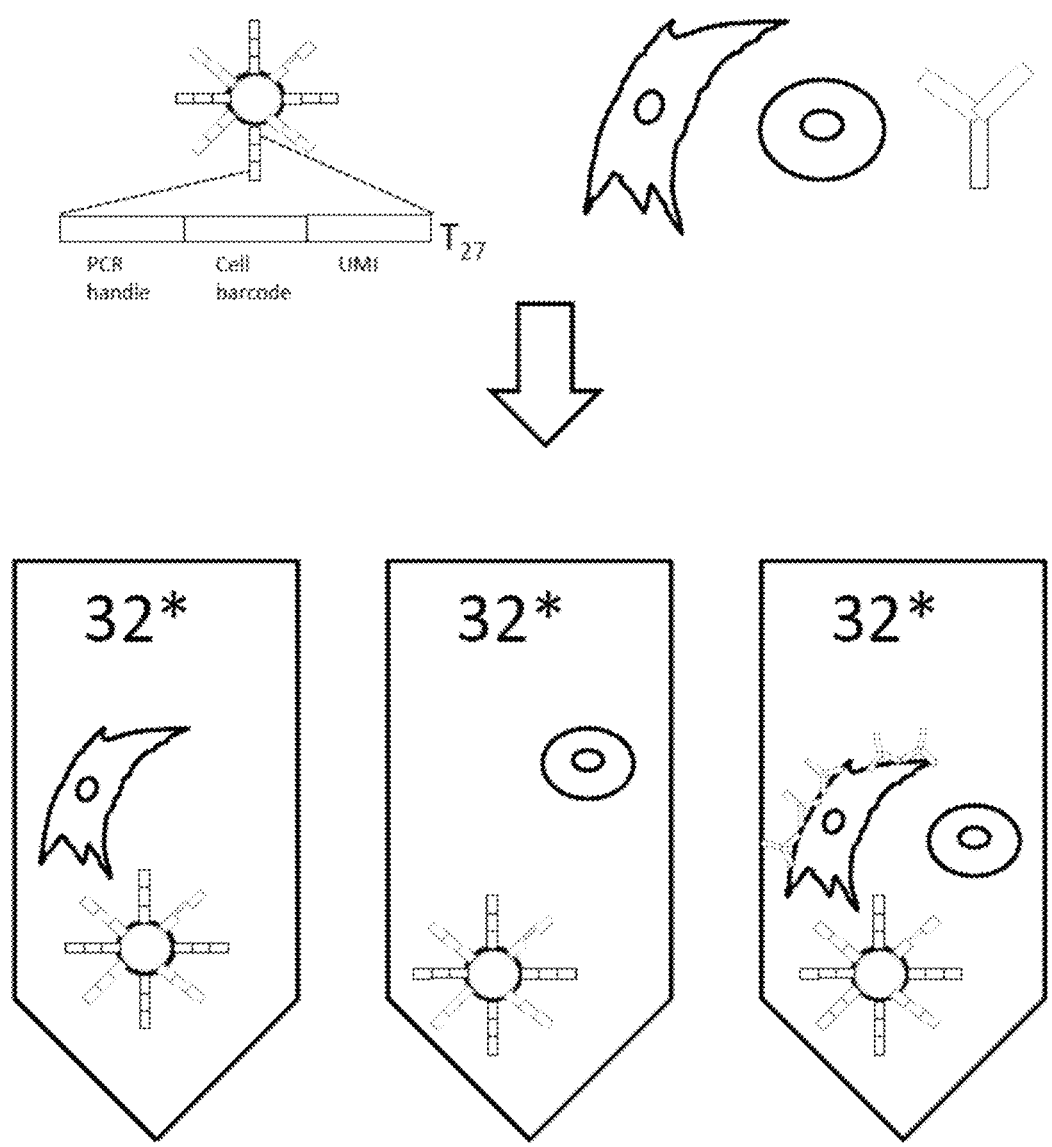

FIG. 3: Setup of 96 different samples. Beads providing differently barcoded primers (top left) are manually pipetted into test tubes together with human SKBR3 cancer cells (elongated shape), murine anti-Her2 hybridoma cells (round shape) or a mixture of both. In the latter case, the human cancer cells were pre-incubated with anti-Her2 antibodies.

Figure 4:
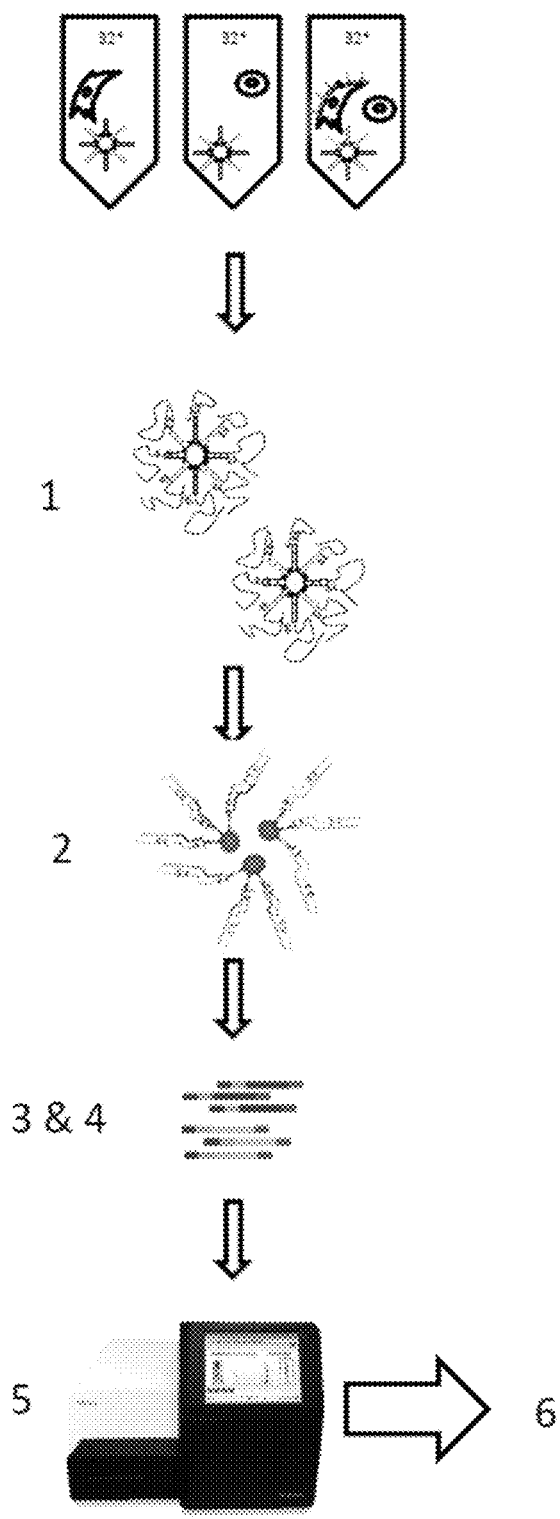

FIG. 4: Sample processing. Cells are lysed and the cellular mRNAs hybridize with the barcoded primers (1). At this stage all beads can be pooled and the samples are processed together for all downstream steps. Reverse transcription with a template switching reverse transcriptase is carried out (2), ensuring that the mRNAs on different beads are differently barcoded. Subsequently a next generation sequencing library is generated including the steps of multiplexing, tagmentation and several purification steps (3-4). Finally the samples are sequenced (5) and the data is analyzed (6). Illustrations for steps (1) and (2) were taken from Macosco et al., Cell, 161(5):1202-14, 2015. doi: 10.1016/j.cell.2015.05.002.

Figure 5:
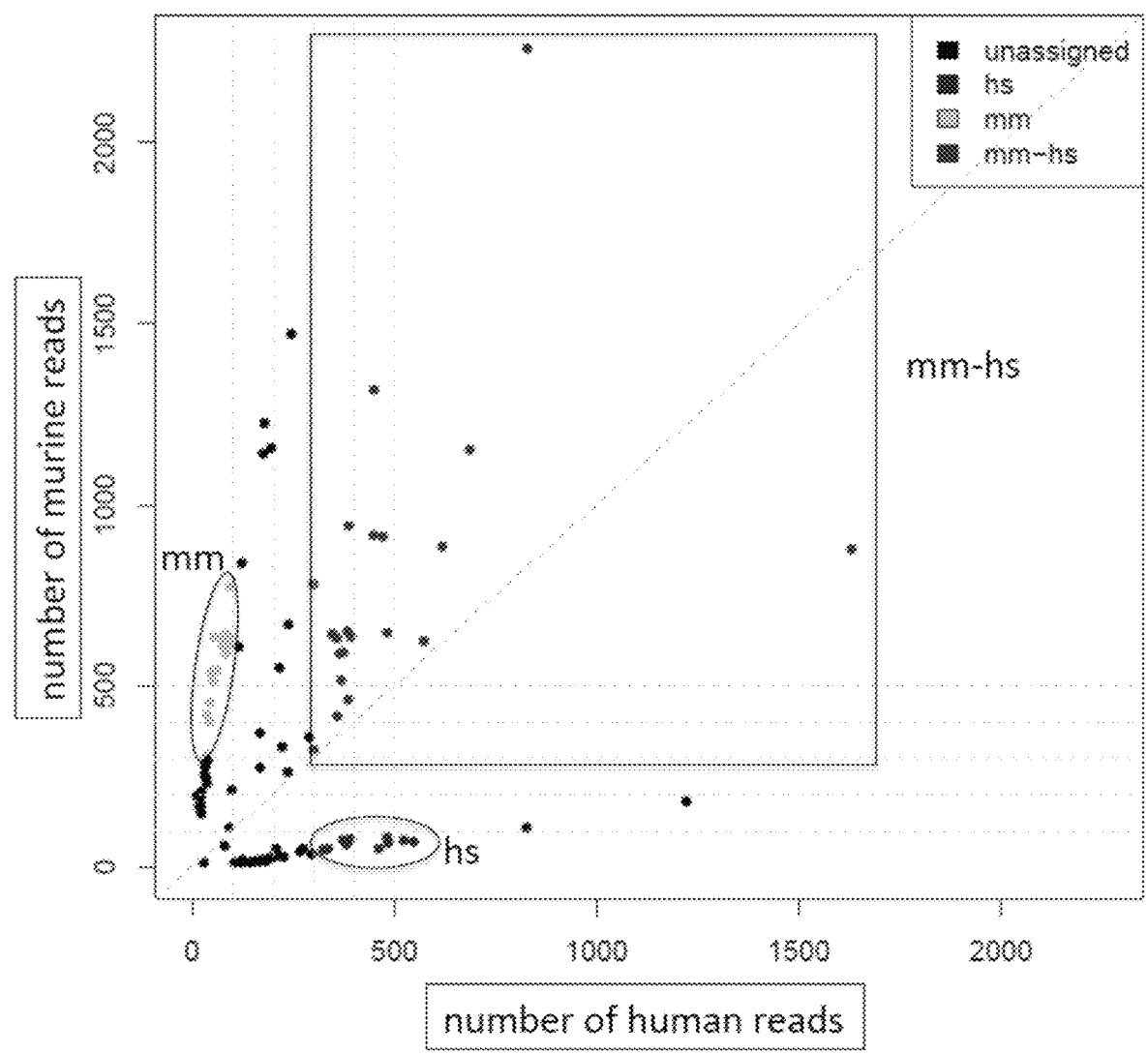

FIG. 5: Results from the sequencing experiment. Each dot corresponds to one sample and its number of human (x-axis) and murine (Y-axis reads). Samples within the ellipse labeled "mm" (left) could be clearly assigned to tubes hosting only a murine hybridoma cell, samples within the ellipse labeled "hs" (bottom) could be clearly assigned to tubes hosting only a human cancer cell and samples within the rectangle could be clearly assigned to tubes hosting both cell types (labeled "mm-hs"). Based on strict threshold algorithms some samples remained unassigned (e.g. when showing less than 300 reads for any species).

DETAILED DESCRIPTION OF THE INVENTION

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", Leuenberger, H. G. W, Nagel, B. and Kölbl, H. eds. (1995), Helvetica Chimica Acta, CH-4010 Basel, Switzerland) and in "Encyclopedia of Microfluidics and Nanofluidics", Springer Reference, Volume 1.

Several documents are cited throughout the text of this specification. Each of the documents cited herein (including all patents, patent applications, scientific publications, manufacturer's specifications, instructions etc.), whether supra or infra, is hereby incorporated by reference in its entirety. Nothing herein is to be construed as an admission that the invention is not entitled to antedate such disclosure by virtue of prior invention.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Throughout this specification and the claims which follow, unless the context requires otherwise, the word "comprise", and variations such as "comprises" and "comprising", are to be understood to imply the inclusion of a stated integer or step or group of integers or steps but not the exclusion of any other integer or step or group of integer or step. As used in this specification and the appended claims, the singular forms "a", "an", and "the" include plural referents, unless the content clearly dictates otherwise.

In a first aspect, the present invention relates to a plurality of microfluidic compartments, wherein at least 1% of said compartments form a subset in which each compartment comprises
(i) a first cell,
(ii) one second cell or one cell-free expression system expressing a polypeptide ligand which is intended to specifically bind to a molecule or part thereof accessible on the surface of the first cell,
(iii) a set of barcode oligonucleotides each comprising a barcode sequence unique to the set and a sequence capable of binding specifically to mRNA and/or cDNA.

The term "plurality" as used herein refers to a number of at least 20, at least 100, at least 1,000 or at least 10,000.

The term "microfluidic compartment" or "microcompartment" as used herein refers to a compartment of a certain size that comprises or encapsulates an aqueous liquid. The size of the microfluidic compartment is usually less than 1 microlitre (μl). Preferably, it is less than 1,000 nl, less than 100 nl, less than 20 nl, or most preferably less than 1 nl. The lower size limit is 1 pl, preferably 10 pl.

A wide variety of compartmentalisation or microencapsulation procedures are available (Benita, S., Ed. (1996). Microencapsulation: methods and industrial applications. Drugs and pharmaceutical sciences. Edited by Swarbrick, J. New York: Marcel Dekker) and may be used to create the microfluidic compartment used in accordance with the present invention. Indeed, more than 200 microencapsulation or compartmentalisation methods have been identified in the literature (Finch, C. A. (1993) Encapsulation and controlled release. *Spec. Publ.-R. Soc. Chem.* 138, 35). These include membrane enveloped aqueous vesicles such as lipid vesicles (liposomes) (New, R. R. C., Ed. (1990). Liposomes: a practical approach. The practical approach series. Edited by Rickwood, D. & Hames, B. D. Oxford: Oxford University Press) and non-ionic surfactant vesicles (van Hal, D. A., Bouwstra, J. A. & Junginger, H. E. (1996). Nonionic surfactant vesicles containing estradiol for topical application. In *Microencapsulation: methods and industrial applications* (Benita, S., ed.), pp. 329-347. Marcel Dekker, New York.). In a preferred embodiment, the microfluidic compartment is selected from the group consisting of droplets, nanowells and valve-based microfluidic compartments. A nanowell is a cavity of any shape and depth. Preferably, it has a diameter of less than two-fold the diameter of a solid particle as defined below so that only individual beads get trapped in the compartment (Fan H C, Fu G K, Fodor S P. *Science.* 347(6222):1258367, 2015. doi: 10.1126/science.1258367). In other words, the diameter of at least 200 nm and of up to 100 μm, preferably of 600 nm to 20 μm. The volume of a nanowell preferably is 1 pL to 10 nL. A valve-based compartment is a section of a microfluidic channel that is closed-off or pinched-off by microfluidic valves (Thorsen T, Maerkl S J, Quake S R, *Science* 298(5593): 580-584, 2002. DOI: 10.1126/science.1076996). The volume of a valve-based compartments preferably is 1 pL to 10 nL Preferably, the microfluidic compartment is a microfluidic droplet of an aqueous liquid in an immiscible liquid. Thus, preferably the microcompartments of the present invention are formed from emulsions; heterogeneous systems of two immiscible liquid phases with one of the phases dispersed in the other as droplets of microscopic size (Becher, P. (1957) Emulsions: theory and practice. Reinhold, New York; Sherman, P. (1968) Emulsion science. Academic Press, London; Lissant, K. J., ed Emulsions and emulsion technology. Surfactant Science New York: Marcel Dekker, 1974; Lissant, K. J., ed. Emulsions and emulsion technology. Surfactant Science New York: Marcel Dekker, 1984). Emulsions may be produced from any suitable combination of immiscible liquids. Preferably the emulsion of the present invention has water (containing a particle and other components) as the phase present in the form of droplets and a hydrophobic, immiscible liquid (preferably an oil) as the surrounding matrix in which these droplets are suspended. Such emulsions are termed 'water-in-oil'. This has the advantage that the aqueous phase is compartmentalised in discrete droplets. The external phase, preferably being a hydrophobic oil, generally is inert. The emulsion may be stabilized by addition of one or more surface-active agents (surfactants). These surfactants act at the water/oil interface to prevent (or at least delay) separation of the phases. Many oils and many emulsifiers can be used for the generation of water-in-oil emulsions; a recent compilation listed over 16,000 surfactants, many of which are used as emulsifying agents (Ash, M. and Ash, I. (1993) Handbook of industrial surfactants. Gower, Aldershot).

Preferably, the aqueous microcompartments are created, handled and/or controlled in a microfluidic system. This technology is based on the manipulation of continuous liquid flow through microfabricated channels. Actuation of liquid flow is implemented either by external pressure sources, external mechanical pumps, integrated mechanical micropumps, or by combinations of capillary forces and electrokinetic mechanisms. Process monitoring capabilities in continuous-flow systems can be achieved with highly sensitive microfluidic flow sensors based on MEMS technology which offer resolutions down to the nanoliter range.

Microfluidic devices typically consist of networks of channels of approximately ten to a few hundred micrometers in diameter into which small quantities of reagents can be injected in a specific sequence, mixed and incubated for a specified time. Assays can be highly parallelized by generating independent compartments using valves (pinching off specific regions of the channels) or two-phase microfluidics, in which aqueous droplets surrounded by an immiscible oil phase serve as closed vessels. These approaches enable drastically reduced assay volumes (pico-nanoliters) and strongly improved throughput. For example, compartments can be generated at rates of more than 1,000 per second. Furthermore, microfluidic modules for the splitting, fusion and sorting of compartments at similar rates have been developed, thus providing a repertoire of manipulations mimicking classical bench top procedures.

In a preferred embodiment (applying to all aspects herein), the device, in particular the channels, is/are large enough to handle compartments comprising eukaryotic cells. In other words, the device, in particular the channels, is/are large enough to handle compartments of the sizes described herein, in particular 660 pl droplets.

In further embodiments, the size of said subset of compartments, i.e. the least 1% of compartments forming a subset in which each compartment comprises the specified components, is at least 2, 3, 4, 5, 6, 7, 8, 9, 10, preferably 13.5% or even more than 20% of the total number of the plurality of compartments, wherein each larger percentage listed is preferred to the next smaller one. In a particular embodiment, the percentage is at least 5%.

Additionally, less than 25%, preferably less than 20% and more preferably less than 15% of the compartments of the plurality of microfluidic compartments form a "blank" subset (when it is referred above or below to a subset, the subset above and not the blank subset is meant) in which the compartments are empty. "Empty" in this respect means that a compartment does not comprise a first cell, a second cell or cell-free expression system, or a set of barcode oligonucleotides as defined above (items (i) to (iii)). A "blank" subset is a subset only comprising such empty compartments.

Each compartment of the subset of the first aspect may comprise more than one first cell, e.g. up to 2, 3, 4, 5, 6, 7, 8, 9 or 10 first cells, wherein lower upper limits are preferred to higher ones. In the most preferred embodiment of the method of the first aspect, each compartment of said subset comprises exactly one first cell.

The term "first cell" as used herein refers to any cell, preferably it is a mammalian cell and more preferably a human cell. In one embodiment, the cell is a stem or pluripotent cell, e.g. an embryonic or adult stem cell, or a non-stem and non-pluripotent cell, preferably in which pluripotency is inducible by a polypeptide ligand. Such a non-stem cell and non-pluripotent cell is preferably a cell derived from the ectoderm, endoderm or mesoderm lineage. Said cell can be selected from the group consisting of growth-arrested cells (e.g. cell which are blocked at various stages of the cell cycle, i.e. G0, G1, S, G2, prophase, prometaphase and metaphase), non-proliferating cells, post- or non-mitotic cells, resting cells, benign cells, senescent cells, in vitro differentiated embryonic stem cells, in vitro differentiated induced pluripotent cells, terminally differentiated cells, and preferably primary cells. Preferred cells are cells selected from the group consisting of adipocytes, astrocytes, B-cells, cardiomyocytes, chondrocytes, cornea epithelial cells, dendritic cells, endocrine cells, endothelial cells, epithelial cells, fibroblasts, glia cells, granulocytes, hematopoietic cells, hematopoietic stem cells, hepatocytes, keratinocytes, intestinal epithelial cells, liver cells, lung epithelial cells type I, lung epithelial cells type II, lymphocytes, macrophages, mammary epithelial cells, melanocytes, mesangial cells, mesenchymal stem cells, muscle cells, myoblast, natural killer cells, neuronal cells, neutrophiles, osteoblasts, pancreatic beta cells, pericytes, preadipocytes, progenitor cells, prostate epithelial cells, renal epithelial cells, renal proximal tubule cells, retinal pigment epithelial cells, sertoli cells, skeletal muscle cells, smooth muscle cells, stem cells, stroma cells, T-cells and subsets of said cell types. Said cells are non-mammalian cells (e.g. from fish or bird species) or mammalian cells (e.g. from mice, rats, monkeys, pigs, dogs, cats, cows, sheep, goats), preferably human cells.

In a preferred embodiment, the first cell is a diseased cell. In particular, the diseased cell may be a tumor cell, a chronically infected cell, a senescent cell, a cell showing an inflammatory phenotype, a cell accumulating amyloid proteins or a cell accumulating misfolded proteins.

In case of a tumor cell, the underlying disease is a tumor, preferably selected from the group consisting of Adrenal Cancer, Anal Cancer, Bile Duct Cancer, Bladder Cancer, Bone Cancer, Brain/CNS, Tumors, Breast Cancer, Cancer of Unknown Primary, Castleman Disease, Cervical Cancer, Colon/Rectum Cancer, Endometrial Cancer, Esophagus Cancer, Ewing Family Of Tumors, Eye Cancer, Gallbladder Cancer, Gastrointestinal Carcinoid Tumors, Gastrointestinal Stromal Tumor (GIST), Gestational Trophoblastic Disease, Hodgkin Disease, Kaposi Sarcoma, Kidney Cancer, Laryngeal and Hypopharyngeal Cancer, Leukemia, Liver Cancer, Lung Cancer, Lymphoma, Lymphoma of the Skin, Malignant Mesothelioma, Multiple Myeloma, Myelodysplastic Syndrome, Nasal Cavity and Paranasal Sinus Cancer, Nasopharyngeal Cancer, Neuroblastoma, Non-Hodgkin Lymphoma, Oral Cavity and Oropharyngeal Cancer, Osteosarcoma, Ovarian Cancer, Pancreatic Cancer, Penile Cancer, Pituitary Tumors, Prostate Cancer, Retinoblastoma, Rhabdomyosarcoma, Salivary Gland Cancer, Sarcoma—Adult Soft Tissue Cancer, Skin Cancer, Small Intestine Cancer, Stomach Cancer, Testicular Cancer, Thymus Cancer, Thyroid Cancer, Uterine Sarcoma, Vaginal Cancer, Vulvar Cancer, Waldnstrom Macroglobulinemia, and Wilms Tumor.

In case of a chronically infected cell, the underlying disease is a chronic infectious disease, such as tuberculosis, malaria, chronic viral hepatitis (HBV, Hepatitis D virus and HCV), Acquired immune deficiency syndrome (AIDS, caused by HIV, Human Immunodeficiency Virus), or EBV related disorders: Systemic Autoimmune Diseases (Systemic Lupus Erithematosus, Rheumatoid Arthritis, and Sjogren Syndrome) and Multiple Sclerosis (MS). Preferably, the chronically infected cell comprises a pathogen or part thereof of the above-recited infectious diseases.

In case of a senescent cell, the underlying disease is a senescence associated disease, such as (i) Rare genetic diseases called Progeroid syndromes, characterized by premature aging: Werner syndrome (WS), Bloom syndrome (BS), Rothmund-Thomson syndrome (RTS), Cockayne syndrome (CS), Xeroderma pigmentosum (XP), Trichothiodystrophy or Hutchinson-Gilford Progeria Syndrome (HGPS) or (ii) Common age related disorders: Obesity, type 2 diabetes, sarcopenia, osteoarthritis, idiopathic pulmonary fibrosis and chronic obstructive pulmonary disease, cataracts, neurodegenerative diseases, or cancer treatment related disorders. Preferably, the senescent cell expresses, in particular in a misfolded form and/or presented on the cell surface, one or more protein such as prion protein (PrP), FasR, Fas ligand, CD44, EGF receptor, CD38, Notch-1, CD44, CD59, or TNF receptor. Notwithstanding, the first cell may also be a non-diseased cell expressing one or more of these proteins.

In case of a cell showing an inflammatory phenotype, the underlying disease is an inflammatory disease, such as an Allergy, Asthma, Artherosclerosis, Autoimmune diseases, Autoinflammatory diseases, Celiac disease, Chronic prostatitis, Glomerulonephritis, Hypersensitivities, Inflammatory Bowel disease, Inflammatory myopathies, Obesity, Pelvic inflammatory disease, Reperfusion injury, Rheumatoid arthritis, Sarcoidosis, Transplant rejection, Vasculitis, or Interstitial cystitis. Preferably, a cell showing an inflammatory phenotype is a cell overexpressing one or more proinflammatory factors such as Bradykinin, C3, C5a, Factor XII, Membrane attack complex, Plasmin, Thrombin, Lysosome granules, Histamine, IFN-gamma, IL-8, IL-6, IL-8, IL-18, Leukotriene B4, Nitric oxide, Prostaglandins, TNF-alpha, or C-reactive Protein.

In case of a cell accumulating amyloid proteins, the underlying disease is a disease associated with the abnormal accumulation of amyloid fibrils such as Alzheimer's disease, Diabetes mellitus type 2, Parkinson's disease, Transmissible spongiform encephalopathy, Fatal familial insomnia, Huntington's disease, Medullary carcinoma of the thyroid, Cardiac arrythmias, Atherosclerosis, Rheumatoid arthritis, Aortic medial amyloid, Prolactinomas, Familial amyloid polyneuropathy, Hereditary non-neuropathic systemic amyloidosis, Dialysis related amyloidosis, Lattice corneal dystrophy, Cerebral amyloid angiopathy Cerebral amyloid angiopathy, Systemic AL amyloidosis, or Sporadic inclusion body myositis. Preferably, a cell accumulating amyloid proteins is a cell overexpressing one or more amyloids such as Beta amyloid, IAPP, Alpha-synuclein, $PrP^{Sc}$, Huntingtin, Calcitonin, Atrial natriuretic factor, Apolipoprotein A1, Serum amyloid A, Medin, Prolactin, Transthyretin, Lysozyme, Beta-2 microglobulin, Gelsolin, Keratoepithelin, Cystatin, Immunoglobulin light chain AL, or S-IBM.

In case of a cell accumulating misfolded proteins, the underlying disease is a proteopathy such as Alzheimer's disease, Cerebral β-amyloid angiopathy, Retinal ganglion cell degeneration in glaucoma, Prion diseases, Parkinson's disease, Tauopathies, Frontotemporal lobar degeneration, FTLD-FUS, Amyotrophic lateral sclerosis, Huntington's disease, Familial British dementia, Familial Danish dementia, Hereditary cerebral hemorrhage with amyloidosis, CADASIL, Alexander disease, Seipinopathies, Familial amyloidotic neuropathy, Senile systemic amyloidosis, AL (light chain) amyloidosis, AH (heavy chain) amyloidosis, AA (secondary) amyloidosis, Type II diabetes, Aortic medial amyloidosis, ApoAI amyloidosis, ApoAII amyloidosis, ApoAIV amyloidosis, Familial amyloidosis of the Finnish type, Lysozyme amyloidosis, Fibrinogen amyloidosis, Dialysis amyloidosis, Inclusion body myositis/myopathy, Cataracts, Retinitis pigmentosa with rhodopsin mutations, Medullary thyroid carcinoma, Cardiac atrial amyloidosis, Pituitary prolactinoma, Hereditary lattice corneal dystrophy, Cutaneous lichen amyloidosis, Mallory bodies, Corneal lactoferrin amyloidosis, Pulmonary alveolar proteinosis, Odontogenic (Pindborg) tumor amyloid, Seminal vesicle amyloid, Cystic Fibrosis, Sickle cell disease, or Critical illness myopathy. Preferably, a cell accumulating misfolded proteins is a cell misfolding one or more proteins such as Amyloid β peptide (Aβ), Tau protein, Amyloid β peptide (Aβ), Amyloid β peptide (Aβ), Prion protein, α-Synuclein, Microtubule-associated protein tau (Tau protein), TDP-43, Fused in sarcoma (FUS) protein, Superoxide dismutase, TDP-43, FUS, Proteins with tandem glutamine expansions, ABri, ADan, Cystatin C, Notch3, Glial fibrillary acidic protein (GFAP), Seipin, Transthyretin, Serpins, Monoclonal immunoglobulin light chains, Immunoglobulin heavy chains, Amyloid A protein, Islet amyloid polypeptide (IAPP; amylin), Medin (lactadherin), Apolipoprotein AI, Apolipoprotein AII, Apolipoprotein AIV, Gelsolin, Lysozyme, Fibrinogen, Beta-2 microglobulin, Amyloid β peptide (Aβ), Crystallins, Rhodopsin, Calcitonin, Atrial natriuretic factor, Prolactin, Keratoepithelin, Keratins, Keratin intermediate filament proteins, Lactoferrin, Surfactant protein C (SP-C), Odontogenic ameloblast-associated protein, Semenogelin I, cystic fibrosis transmembrane conductance regulator (CFTR) protein, Hemoglobin, or Hyperproteolytic state of myosin ubiquitination.

In a preferred embodiment of the first aspect, the first cell is the same or of the same cell type (e.g. a tumour cell) for each compartment.

The term "second cell" as used herein refers to a cell secreting the polypeptide ligand or presenting the polypeptide ligand on its surface. It is preferred that the second cell is of the same cell type within the plurality of compartments. In particular, the second cell is a cell of the B-cell lineage, preferably a plasma cell. Most preferably, the cell of the B-cell lineage is derived from a vertebrate immunized with the first cell or one or more molecules or parts thereof accessible on the surface of the first cell, for example membrane extracts. In another embodiment, the second cell is a cell expressing a polypeptide ligand derived from a library.

The term "cell-free expression system" as used herein refers to a combination of molecules necessary for producing protein from an input RNA or DNA, such as a plasmid. The combination may comprise ribosomes, tRNAs, amino acids, including amino acyl tRNAs, RNA polymerase, ribonucleotides, and any necessary cofactors, buffering agents and salts that are required for enzymatic activity, and may include a cell lysate. Examples of cell-free expression systems include, but are not limited to, cell-free extracts of bacteria (like *E. coli*) or eukaryotic cells (like rabbit reticulocytes) containing transcription and translation systems required to produce mRNA (if the input is DNA) and protein. Specific examples of cell-free expression systems are the Expressway™ Plus expression system supplied by Invitrogen (Carlsbad, CA, USA) or the reticulocyte lysate system supplied by Roche Diagnostics (Mannheim, Germany). The scope of a cell-free expression system herein, e.g. when it is referred to "a" cell-free expression system or "one" cell-free expression system is determined by the polypeptide ligand it expresses. In other words, a cell-free expression system is a single cell-free expression system if it comprises input RNA or DNA for only one polypeptide ligand.

In a preferred embodiment of the first aspect, the polypeptide ligand expressed by each second cell or cell-free expression system has a constant region and a variable region. Therein, the variable region usually determines the binding specificity and the constant region provides the framework. Further, it is preferred that the polypeptide ligand of each second cell or cell-free expression system has the same constant region. Generally, the plurality of microfluidic compartments comprises different polypeptide ligands, in particular peptide ligands with different variable regions.

In one embodiment, the polypeptide ligand is selected from the group consisting of an antibody, an antibody derivative and an antibody mimetic. The antibody, antibody derivative or antibody mimetic may be mono-specific (i.e. specific to one target molecule or part thereof accessible on the surface of a cell) or multi-specific (i.e. specific to more than one target molecule or part thereof accessible on the surface of the same or a different cell), for example bi-specific or tri-specific (see, e.g., Castoldi et al., Oncogene. 2013 Dec. 12; 32(50):5593-601; Castoldi et al., Protein Eng Des Sel. 2012 October; 25(10):551-9).

The term "antibody derivative" as used herein refers to a molecule comprising at least one antibody variable domain, but not having the overall structure of an antibody such as IgA, IgD, IgE, IgG, IgM, IgY or IgW, although still being capable of binding a target molecule. Said derivatives may be, but are not limited to functional (i.e. target binding, particularly specific target binding) antibody fragments such as Fab, Fab2, scFv, Fv, or parts thereof, or other derivatives or combinations of the immunoglobulins such as nobodies, diabodies, minibodies, camelid single domain antibodies, single domains or Fab fragments, domains of the heavy and light chains of the variable region (such as Fd, VL, including Vlambda and Vkappa, VH, VHH) as well as mini-domains consisting of two beta-strands of an immunoglobulin domain connected by at least two structural loops. Preferably, the antibody derivative is monovalent.

The term "antibody mimetic" as used herein refers to organic compounds that, like antibodies, can specifically bind antigens, but that are not structurally related to antibodies. They are usually artificial peptides or proteins with a molar mass of about 3 to 20 kDa. Non-limiting examples of antibody mimetics are affibodies, affilins, affimers, affitins, anticalins, avimers, DARPins, fynomers, Kunitz domain peptides, monobodies, Z domain of Protein A, Gamma B crystalline, ubiquitin, cystatin, Sac7D from *Sulfolobus acidocaldarius*, lipocalin, A domain of a membrane receptor, ankyrin repeat motive, SH3 domain of Fyn, Kunits domain of protease inhibitors, the $10^{th}$ type III domain of fibronectin, synthetic heterobivalent or heteromultivalent ligands (Josan et al., Bioconjug Chem. 2011 22(7):1270-1278; Xu et al., PNAS 2012 109 (52) 21295-21300; Shallal et al., Bioconjug Chem. 2014 25(2) 393-405) or synthetic peptide ligands, e.g. from a (random) peptide library. Synthetic peptide ligands have non-naturally occurring amino acid sequences that function to bind a particular target molecule. Peptide ligands within the context of the present invention are generally constrained (that is, having some element of structure as, for example, the presence of amino acids which initiate a β turn or β pleated sheet, or for example, cyclized by the presence of disulfide bonded Cys residues) or unconstrained (linear) amino acid sequences of less than about 50 amino acid residues, and preferably less than about 40 amino acids residues. Of the peptide ligands less than about 40 amino acid residues, preferred are the peptide ligands of between about 10 and about 30 amino acid residues.

The term "intended to specifically bind" as used herein refers to potential binding reaction that is intentional or desired. It is not an accidental binding reaction that may occur because a second cell or cell-free expression system happens to express a polypeptide binding to a molecule or part thereof accessible on the surface of the first cell, which may occur by co-compartmentalizing of a first cell and a second cell or cell-free expression system by pure chance or accident. Intended means, for example, that the co-compartmentalizing is performed as part of a screen which is designed to identify polypeptide ligands which bind to a molecule or part thereof accessible on the surface of the first cell and/or trigger a certain, in particular a desired effect on gene expression of the first cell. In one embodiment and in particular in the embodiment in which the second cell is derived from immunization of an animal with the first cell as described herein, it is preferred that the subset of compartments referred to herein (e.g. the at least 5%, 10%, 13.5% or 20% subset) comprises one second cell or one cell-free expression system expressing a polypeptide ligand that does in fact specifically bind to a molecule or part thereof accessible on the surface of the first cell. In the embodiment described herein in which polypeptide ligands from a library not specific for the first cell are used, however, it is likely that not all polypeptide ligands expressed by the second cells or cell-free expression systems of said compartment subset specifically bind to a molecule or part thereof accessible on the surface of the first cell. Nevertheless, they are still intended to.

The term "specifically binds" as used herein refers to a binding reaction which is determinative of the presence of the binding partner, in this case the molecule or part thereof accessible on the surface of the first cell, in a heterogeneous population of such binding partners and, in particular, cells, such as in an organism, preferably a human body. As such, the specified ligand binds to its particular target molecule and does not bind in a substantial amount to other molecules present on cells or to other molecules to which the ligand may come in contact in an organism. Generally, a ligand that "specifically binds" a target molecule has an equilibrium affinity constant greater than about $10^5$ (e.g., $10^6$, $10^7$, $10^8$, $10^9$, $10^{10}$, $10^{11}$, and $10^{12}$ or more) mole/liter for that target molecule.

In one embodiment, regarding the target molecule or part thereof accessible on the surface of the first cell, the target molecule is a cellular receptor, more preferably a cell signaling receptor. Preferably, it is selected from the group consisting of a protein, a glycolipid or a glycoside. In a particular embodiment, the target molecule is a protein selected from the group consisting of a G-protein coupled receptor, an ion channel and a cross-membrane transporter.

The term "barcode oligonucleotide" as used herein refers to an oligonucleotide having at least one so-called variable region ("barcode sequence"), the nucleotide sequence of which is the same within the same set of oligonucleotides compared to barcode oligonucleotides of other sets used. "Variable" therein means not that the sequence of a particular oligonucleotide can change, but that there are oligonucleotides which are identical in structure and sequence with the exception of the sequence of the variable regions, i.e. the variable regions are different between oligonucleotides that are otherwise identical in structure and sequence. The length of the variable region, is preferably 1 to 50 nucleotides, more preferably 1 to 20 nucleotides and most preferably 2 to 10 nucleotides. The overall length of the "barcode oligonucleotide" is preferably 10 to 100 nucleotides, more preferably 10 to 50 nucleotides and most preferably 10 to 25 nucleotides.

In a preferred embodiment, the barcode oligonucleotide further comprises a unique molecular identifier (UMI). A "UMI" is an oligonucleotide sequence which is unique (or random with a length that makes uniqueness likely) for each oligonucleotide molecule of all oligonucleotides in a set and/or all oligonucleotides linked to a solid particle. This can improve reliability of amplification and reduce amplification noise (see, e.g. S. Islam et al., Quantitative single-cell RNA-seq with unique molecular identifiers. *Nature methods* 11, 163, February, 2014). Also, UMIs can be used to digitally count the mRNA transcripts after sequencing. Therein, preferably, all sequenced amplificates having the same barcode sequence and the same UMI are counted as one, i.e. a single event or single mRNA transcript. To achieve uniqueness of the UMIs, their diversity $4^N$ (N being the number of nucleotides per UMI) is preferably at least 10 times larger than the number of compartments in the subset as defined above, preferably than the number of compartments in the plurality of microfluidic compartments.

The term "set of barcode oligonucleotide" as used herein refers to a plurality of barcode oligonucleotides having the same barcode sequence and preferably each a UMI unique within the set and/or within the barcode oligonucleotides linked to a solid particle. In a preferred embodiment, each set of barcode oligonucleotides is linked to one or more, preferably one solid particle, preferably a bead or a nanoparticle. If it is linked to more than one solid particle, each solid particle preferably comprises the complete set, i.e. the solid particles are preferably identical copies of each other, wherein each copy comprises the complete set. Most preferably the solid particle is a bead. A "bead" (also termed "microbead") is a uniform polymer particle with a diameter of at least 100 nm and of up to 50 μm, preferably of 300 nm to 10 μm, and with a surface to which nucleic acids can bind or be coupled. A round shape is not required, i.e. the term "bead" as used herein also encompasses other shapes. The beads referred to herein are usually polyethylene or polystyrene beads or beads made of gel matrices. The term "nanoparticle" used herein refers to a particle having a diameter of from about 1 to 1000 nm, preferably 1 to 100 nm. Components of the nanoparticle may include metal such as gold, silver, copper, aluminum, nickel, palladium, platinum, alloys thereof, a semiconductor material such as CdSe, CdS, InAs, InP, or core/shell structures thereof, or organic particles such as particles made from organic polymer, lipids, sugars, or other organic materials, e.g. polystyrene, latex, acrylate, or polypeptide. Such organic particles may optionally contain some inorganic material; however, the amount of inorganic material is less than 50%, less than 25%, less than 10%, less than 5%, or less than 1%.

The term "sequence capable of binding specifically to mRNA and/or cDNA thereof" as used herein refers to a sequence that is at least 80%, preferably at least 90%, more preferably at least 95% and most preferably 100% complementary to a given mRNA and/or cDNA thereof. With respect to mRNA, it is preferred that said sequence is a sequence capable of binding specifically to an mRNA 3' poly(A) tail, in particular a poly(dT) sequence or a poly(dU) sequence. Such a sequence is capable of binding specifically to any mRNA and is usually 10-60 nucleotides long, preferably 15-30 and more preferably about 20 nucleotides long.

For binding to a specific mRNA and/or cDNA, the sequence capable of binding specifically to mRNA and/or cDNA thereof is capable of binding to a gene-specific sequence (the gene the mRNA is transcribed from) of the mRNA or cDNA. Such a sequence is usually 10-60 nucleotides long, preferably 15-30 and more preferably 15-25 nucleotides long.

Generally, it is preferred that the sequence capable of binding specifically to mRNA and/or cDNA thereof is at the 3' end of the barcode oligonucleotide and is capable of priming a DNA polymerisation, either from an mRNA template or a cDNA template. If the sequence is capable of binding to a gene-specific sequence, it is preferred that the compartments of said subset further comprise a further oligonucleotide forming a primer pair with said sequence that is capable of binding to a gene-specific sequence, wherein the primer pair is suitable for generating a DNA amplicon from the mRNA and/or cDNA thereof. In a preferred embodiment, the sequence capable of binding specifically to mRNA and/or cDNA thereof is the same for each barcode oligonucleotide of the set.

In a preferred embodiment of the plurality of compartments of the first aspect, the first cell and the second cell or polypeptide ligand expressed by the cell-free expression system are derived from different species. Preferably, the first cell is a mammalian cell, e.g. a mouse, rat or primate cell. Most preferably it is a human cell. The second cell or the genes expressed by the cell-free expression system are from a different species, including eukaryotic (e.g. yeast or insect) and prokaryotic (e.g. *E. coli*) species. In a particular embodiment, it is from a vertebrate species, in particular a mammalian species. Particular examples of species are primate species, rabbit, mouse, rat, camel and shark.

The second cell may also be a cell genetically engineered to express the polypeptide ligand. In this particular case, the second cell may or may not be of the same species as the first cell being for example a human cell, but the polypeptide ligand expressed is derived from a different species than the first cell, e.g. a non-human species if the first cell is a human cell. In a particular embodiment, the second cell is genetically engineered to express a polypeptide ligand from a library The term "library" as used herein refers to a collection of polypeptides usually used for screening purposes, in particular of polypeptide ligands as defined herein. The term encompasses a collection of DNA fragments that encode the collection of polypeptides and is maintained in DNA form for purposes of storage and propagation, for example within a population of micro-organisms including bacteria, viruses and phages. It also encompasses a collection of cells expressing the collection of polypeptides.

In another preferred embodiment, the second cells or the cell-free expression systems within the plurality of compartments have a uniform expression pattern. The term "uniform expression pattern" refers to a gene expression that is substantially the same and differs substantially only with respect to the type of polypeptide ligand expressed, in particular regarding its variable region but not its constant region. "Substantially the same" herein means a variation of no more than 10 times, preferably 5 times and preferably 3 times the technical noise observed for a single cell analysis. The term "technical noise" refers to the variation observed for at least replicates of determining the gene expression of a single cell. The technical noise can be determined, for example, as described in Brennecke et al., Nature Methods, vol. 10, no. 11, p. 1093.

In yet another embodiment, the compartments of said subset of the plurality of compartments of the first aspect each further comprise one or more of the following:
- a cell lytic agent,
- an RNase-inhibitor,
- a DNase,
- reagents for a reverse transcription reaction, and/or
- a drug or drug candidate for treating the diseased cell or the disease the diseased cell is derived from, wherein the diseased cell it the first cell. Such a drug can be used to screen for polypeptide ligands which influence the sensitivity of the first cell to the drug, e.g. which act as a sensitizer.

Reagents for a reverse transcription reaction preferably comprise a reverse transcriptase, aqueous buffers, salts and/or desoxynucleoside triphosphates. Suitable reagents are well known in the art, see, e.g., Molecular Cloning: A Laboratory Manual (4$^{th}$ Edition), Green & Sambrook 2012. Preferred are thermostable RNA polymerases, preferably in the presence of a RNA-dependent DNA polymerase including, without limitation, AMV, Cloned MMLV, Superscriptll, ReverTraAce, Tth reverse transcriptase, hepatitis B reverse transcriptase, cauliflower mosaic virus reverse transcriptase, bacterial reverse transcriptase, Thermoscript. RSV reverse transcriptase, RAV (Rous-associated virus) reverse transcriptase, MAV (myeloblastosis-associated virus) reverse transcriptase, and HIV reverse transcriptase. See Kotewicz M, et al., U.S. Pat. No. 5,244,797, and Gerard G, et al., WO1998047912. Preferably, they also comprise constant Smart-primers for the incorporation of specific 5' oligonucleotides during cDNA synthesis. These Smart-primers make use of a 3'-poly-C stretch unspecifically introduced into all newly synthesized cDNA molecules by some reverse transcriptases (e.g. the Moloney murine leukemia virus reverse transcriptase) during the first strand synthesis, based on its terminal transferase activity. The Smart primers consist of a sequence of interest (e.g. the T7 oligonucleotide sequence) plus a short poly-G stretch on their 3'-end hence allowing to partially hybridize with the cDNA molecules. When the RT reaches this point, it switches template and incorporates a sequence complementary to the remaining Smart primer sequence into the newly synthesized cDNA strand. Hence each cDNA molecule, independently of the gene it encodes, has defined sequences on both ends (poly-T and the complementary Smart primer sequence) and can thus be amplified by subsequent PCR.

In a second aspect, the present invention relates to a method for generating a plurality of microfluidic compartments according to the first aspect, comprising the steps of:
(a) introducing into a microfluidic system: (i) a fluid comprising a plurality of first cells, (ii) a fluid comprising a plurality of second cells or cell-free expression systems each expressing a polypeptide ligand which is intended to specifically bind to a molecule or part thereof accessible on the surface of a first cell, and (iii) a fluid comprising sets of barcode oligonucleotides, wherein the barcode oligonucleotides of each set comprises a barcode sequence unique to the set, and a sequence capable of binding specifically to mRNA and/or cDNA,
(b) repeatedly co-compartmentalizing a first cell, a second cell or cell-free expression system, and a set of barcode oligonucleotides into microfluidic compartments, such that the size of the subset of compartments in the plurality of compartments is at least 1%.

In a particular embodiment, the size of the subset of compartments in the plurality of compartments is at least 5% (other percentages as specified with respect to the first aspect are also envisaged).

The term "fluid" as used herein refers to an aqueous liquid if the components it comprises are not comprised in a microfluidic droplet. If they are comprised in an aqueous miccrofluidic droplet, the liquid is an immiscible liquid as defined above.

The term "co-compartmentalizing" as used herein refers to bringing together two or more components in a single compartment, in particular a microfluidic compartment as defined above. With respect to microfluidic droplets, is can also be referred to as "co-encapsulating", which as used herein refers to the embedding of components in an aqueous phase into an aqueous microfluidic droplet in an immiscible phase. Encapsulation or microencapsulation procedures are described above. With respect to the present invention, the term "co-encapsulating" is also to be understood as encompassing the embedding of the components of two or more aqueous microfluidic droplets into a single aqueous microfluidic droplet. This process is also known as droplet fusion. One-to-one fusion can be achieved, e.g., according to Mazutis et al. (Lab Chip (2009) vol. 9 (18) pp. 2665-2672). If one-to-one fusion is applied and more than two droplets are fused, the droplets are fused sequentially. Further droplet fusion methods are described in P. Day et al. (eds.), Integrated Analytical Systems, Springer Science+Business Media, LLC 2012, Chapter 2.

In a preferred embodiment, the desired size of said subset is achieved by
(a) passive co-compartmentalizing, preferably co-encapsulation, wherein the compartment volume and the cell concentration of (i), the cell concentration or cell-free expression system concentration of (ii), and the set concentration of (iii) are selected such that λ is between 0.1 and 2, preferably about 1 for each of the cell concentration of (i), the cell concentration or cell-free expression system concentration of (ii), and the set concentration of (iii), wherein λ is the average number of cells, cell-free expressions systems and sets, respectively, per compartment, (alternatively or additionally, if the fluids (i) and (ii) are combined prior to co-encapsulation, λ is between 1 and 3, preferably about 2 for the concentration of all first cells and second cells or cell-free expressions systems),
(b) deterministic co-compartmentalizing, preferably co-encapsulation, wherein the channel geometry facilitates an alignment of a first cell, a second cell or cell-free expression system, and/or a set of barcode oligonucleotides to achieve a co-compartmentalizing that is improved over a Poisson-determined co-compartmentalizing.

Methods for passive co-compartmentalizing are described for example in Clausell-Tormos et al., Chem Biol. (5):427-37, 2008 and Todd et al., RSC Adv., 3, 20512-20522, 2013. To achieve λ between 1 and 3, preferably about 2 for the concentration of all first cells and second cells or cell-free expressions systems, it is preferred that a density of cells/cell-free expressions systems combined of 0.5 to 10×10E6 per ml, preferably 1 to 3×10E6 per ml, is used. To improve passive co-compartmentalizing, the droplets can be sorted and selected for the correct droplet occupancy. In other words, the presence of a first cell, a second cell or cell-free expression system, and/or a set of barcode oligonucleotides in the compartments is detected and the compartments are sorted for the presence of a first cell, a second cell or cell-free expression system, and/or a set of barcode oligonucleotides. Suitable selection and sorting procedures are described in Hu et al., Lab Chip, 2015,15, 3989-3993; DOI: 10.1039/C5LC00686D. Methods for deterministic co-compartmentalizing are described, for example, in Kemna et al., Lab Chip. 2012 12(16):2881-7; doi: 10.1039/c21c00013j. A suitable channel geometry for deterministic co-compartmentalizing is for example a spiral channel that uses dean force as also described in Kemna et al.

In another embodiment of the method of the second aspect, in step (b) the first cells, second cells or cell-free expression systems and sets of barcode oligonucleotides are comprised individually in microfluidic compartments, preferably droplets, prior to step (b) and the co-compartmentalizing in step (b) is by compartment, preferably droplet, fusion, or wherein in step (b), the first cells, second cells or cell-free expression systems and sets of barcode oligonucleotides are not comprised in microfluidic compartments prior to co-localizing and compartments, preferably droplets, are generated in step (b).

Droplets can be generated by creating a stream of monodispersed water or oil droplets in an immiscible phase. Microfluidic droplet generators work by combining two or more streams of immiscible fluids and generating a shear force on the discontinuous phase causing it to break up into discrete droplets. Preferred droplet generators are focused-flow droplet generators and T-shaped droplet generators. Focused-flow droplet generators are based on a continuous phase fluid (focusing or sheath fluid) flanking or surrounding the dispersed phase (focused or core fluid), so as to give rise to droplet break-off in the vicinity of an orifice through which both fluids are extruded. T-shaped droplet generators use a microchannel T-junction, at which droplets are spontaneously formed at the intersection, taking advantage of the interface instability between oil and aqueous streams each coming from one direction towards the junction.

All other terms used with respect to the second aspect have the meanings as defined with respect to the first aspect of the invention. Further, all embodiments specified for the first aspect that are applicable to the second aspect are also envisaged for the second aspect.

In a third aspect, the present invention relates to a method for determining the gene expression of a cell, comprising the steps:
 (a) providing a plurality of microfluidic compartments according to the first aspect,
 (b) lysing the cells comprised in the compartments,
 (c) reverse transcribing mRNA released from the cells to cDNA,
 (d) amplifying the cDNA,
 (e) determining the sequence and optionally the respective amount of the cDNA, and
 (f) selecting sequences comprising the same barcode sequence, wherein the following sequences are excluded:
  sequences derived from a second cell or a cell-free expression system,
  sequences comprising a unique barcode sequence that is not associated in other sequences with a nucleotide sequence encoding for a polypeptide ligand expressed by a second cell or a cell-free expression system,
  sequences comprising a unique barcode sequence that is associated with a nucleotide sequence encoding for more than one polypeptide ligand expressed by a second cell or a cell-free expression system, wherein step (c) or step (d) is carried out with a barcode oligonucleotide as a primer.

In a preferred embodiment, the method comprises comparing the gene expression of a first cell not contacted with a polypeptide ligand with the gene expression determined in said method. The gene expression of a first cell not contacted with a polypeptide ligand may either be already known or pre-determined, or it may be determined as a control using steps (b) to (e) of the method of the third aspect on a provided compartment comprising a known number of first cells, preferably one first cell. Using the gene expression of a first cell not contacted with a polypeptide ligand in this way facilitates the determination of changes in gene expression caused by a polypeptide ligand.

The term "determining the gene expression of a cell" as used herein refers to determining the mRNA produced by a cell. This can be a specific mRNA transcript (i.e. of one specific gene) or all mRNAs, broken down to the sequence, in other words the transcriptome of a cell (i.e. the collection of mRNA produced from a DNA genome). Preferably, the amount of the mRNA is determined as well, e.g. using an UMI.

The term "lysing" as used herein refers to the disruption of the membrane of the cell such that the RNA of the cell is accessible to barcode oligonucleotides within the same compartment. The cell can be lysed by any suitable means which does not disrupt the integrity of the compartment, in particular of a droplet. Suitable means are, for example, heat, cycles of freezing and thawing, laser irradition, sonication, mechanical lysis, e.g. shearing, or adding a lysis buffer (e.g. fusing the droplet with a microfluidic droplet comprising a lysis buffer). Preferred means are cycles of freezing and thawing or laser irradition. In a microfluidics setting, heat lysis can be achieved via a flat metal plate mounted under a microfluidic chip, which is in thermal connection with the samples. By using glass slides embedded in the PDMS, or pre-soaking the chip in water, evaporation problems are ruled out. Alternatively, heat lysis can be achieved by using heating elements integrated into a microfluidic chip.

In step (c), the mRNA is transcribed using methods known in the art, e.g. from Molecular Cloning: A Laboratory Manual ($4^{th}$ Edition), Green & Sambrook 2012. Reagents for a reverse transcription reaction are described above.

Although the method already implies this, it is noted that if the compartments comprise cell-free expression systems, the mRNA of these cell-free expression systems is also reverse transcribed to cDNA in step c).

In step (d), the cDNA/DNA is amplified by methods known in the art, e.g. from Molecular Cloning: A Laboratory Manual ($4^{th}$ Edition), Green & Sambrook 2012. Reagents for amplifying cDNA preferably comprise a polymerase, e.g. a DNA polymerase, aqueous buffers, salts, desoxynucleotide triphosphates and/or primers. Suitable reagents are well known in the art, see, e.g., Molecular Cloning: A Laboratory Manual ($4^{th}$ Edition), Green & Sambrook 2012. The cDNA may be amplified directly, e.g. using any PCR based method, or indirectly, e.g. by in vitro transcription (IVT) amplification (see, e.g., Hashimshony et al., Cell Reports, 2, 666-673, 2002), wherein the cDNA is transcribed again to obtain a plurality of mRNA molecules, which are then transcribed to cDNA again. Preferably, the template cDNA/DNA is amplified by a factor of $2^{5-30}$, more preferably $2^{10-25}$, which corresponds to about 5-30 or 10-15 PCR cycles. For indirect amplification methods such as IVT amplification, the incubation time and/or the amount of enzyme for transcription are adjusted accordingly. If not already comprised, reagents for amplifying an oligonucleotide (as defined herein) are added in the amplification step.

In step (e), the sequence of the cDNA (and thereby the sequence of the corresponding mRNA) can be determined by any sequencing method known in the art (see, e.g. Molecular Cloning: A Laboratory Manual ($4^{th}$ Edition), Green & Sambrook 2012). Exemplary sequencing reactions include those based on techniques developed by Maxam and Gilbert (Proc. Natl. Acad Sci USA, 1977, 74:560) or Sanger (Sanger et al., 1977, Proc. Nat. Acad. Sci. USA, 74:5463). It is also contemplated that any of a variety of automated sequencing procedures may be utilized (Biotechniques (1995) 19:448), including sequencing by mass spectrometry. See, for example, U.S. Pat. No. 5,547,835 and international patent publication number WO 94/16101, U.S. Pat. No. 5,547,835 and international patent application number WO 94121822 and U.S. Pat. No. 5,605,798 and International Patent Application No. PCT/US96/03651; Cohen et al. (1996) Adv. Chromatogr. 36: 127-162; and Griffin et al. (1993) Appl Biochem Biotechnol 38:147-159. Yet other suitable sequencing methods are disclosed, for example, in U.S. Pat. Nos. 5,580,732 and 5,571,676.

In a preferred embodiment, it is determined by Next Generation Sequencing (NGS, also known as $2^{nd}$ or $3^{rd}$ generation sequencing). The concept behind NGS it that the bases of a small fragment of DNA are sequentially identified from signals emitted as each fragment is re-synthesized from a DNA template strand. NGS extends this process across millions of reactions in a massively parallel fashion, rather than being limited to a single or a few DNA fragments. This advance enables rapid sequencing of large stretches of DNA base pairs spanning entire genomes, with the latest instruments capable of producing hundreds of gigabases of data in a single sequencing run. See, e.g., Shendure and Ji, *Nature Biotechnology* 26, 1135-1145 (2008) or Mardis, Annu Rev Genomics Hum Genet. 2008; 9:387-402. Suitably NGS platforms are available commercially, e.g. the Roche 454 platform, the Roche 454 Junior platform, the Illumina HiSeq or MiSeq platforms, or the Life Technologies SOLiD 5500 or Ion Torrent platforms.

In a preferred embodiment of step (e), cDNA sequences and their respective amount are determined, i.e. the amount of each unique cDNA sequence prior to the amplification of step (d). This reflects the amount of mRNA present in each compartment. Preferably, the amount is determined using UMIs, i.e. by digitally counting the sequences associated with the same UMI.

The selection of sequences in step (0 is performed by a suitable in silico process, such as The Galaxy Project (www.galaxyproject.org)

The term "associated" as used herein refers to a linkage in a nucleic acid sequence as a result of being reversed transcribed or amplified with a respective barcode oligonucleotide as a primer.

The use of a barcode oligonucleotide as a primer in step (c) or step (d) depends on the structure of the barcode oligonucleotide as described above. If, for example, the barcode oligonucleotide has a poly(dT) or poly(dU) sequence, it is used as a primer for the reverse transcription of step (c). If it is part of a primer pair, it is used as a primer for the cDNA amplification in step (d).

In one embodiment of the method of the third aspect, in step (a) the plurality of microfluidic compartments is provided using the method of the second aspect.

Preferably, in the method of the third aspect, the contents of the compartment are pooled, preferably after annealing of the barcode oligonucleotide primer and at any stage prior to step (f), (e), (d) or (c), with increasing preference and considering the below limits for mRNA and cDNA. The annealing occurs within the compartments after lysing the cells (although for mRNA produced by cell-free expression systems it may occur before). If the barcode oligonucleotide is designed to anneal to mRNA, the contents of the compartments are preferably pooled after, with decreasing preference, step (b), (c) or (d). If the barcode oligonucleotide is designed to anneal to cDNA, the contents of the compartments are preferably pooled after step (d). Generally, the pooling of the contents of the compartments occurs as soon as possible to allow parallel processing for saving time and resources. For this purpose, it is intended that the contents of the compartments are pooled prior to the sequencing in step (e).

In the embodiment of the compartments being microfluidic droplets, the pooling of the contents of the droplets occurs by pooling the droplets and subsequently breaking the droplets. Preferably, the droplets are pooled after step (a), (b) or (c), or the plurality of droplets is already provided as pooled droplets. While the pooling of the droplets always occurs prior to breaking them, it does not have to occur immediately prior to breaking, i.e. one or more of the steps of the method of the third aspect may occur between pooling and breaking of the droplets. Pooled (i.e. collected) droplets are broken by using any means known in the art, for example by addition of a destabilising agent, for example using an emulsion destabilizer such as perfluoro-octanol or A104 (RainDance Technologies) as described in Clausell-Tormos et al. (Chem Biol, vol 15, pg 427, 2008), or by the application of an electric field, or by freezing and thawing the emulsion, to release the combined components into the aqueous phase. In yet another embodiment, this can be achieved by injecting the droplets into a reservoir (and optionally adding a emulsion destabilizer) where the phases separate due to their different densities. Then the upper aqueous phase is removed for further processing. The contents of the pooled compartments, preferably droplets, can be carried out in conventional bench-top setting.

The sequences from a second cell or cell-free expression system can be excluded, for example, as follows:
1) In a preferred embodiment, the first and the second cells or genes (in particular polypeptide ligands) expressed by the cell-free expression systems are from different species and sequences derived from a second cell or the cell-free expression system are excluded based on sequence variations between the species.
2) In an alternative embodiment, wherein the second cell or cell-free expression system has a uniform expression pattern, the mean expression of all genes of the uniform expression pattern is determined and subtracted from the gene expression determined in step (e). The remaining gene expression is that of the first cell. Preferably, the mean expression of all genes of the uniform expression pattern is determined on a single cell level for at least 3 second cells or cell-free expression systems. The uniform expression pattern comprises the sequences of all mRNAs (of which the cDNAs were sequenced) and their respective amounts.

In a further preferred embodiment of the method of the first aspect, the method further comprises a step (g) of determining which polypeptide ligand was comprised in the same compartment as the cell from which the sequences selected in step (f) are derived from, comprising identifying, from the excluded sequences derived from a second cell or a cell-free expression system, the nucleic acid sequence encoding for a polypeptide ligand which is associated with the barcode sequence of the selected sequences of step (f). Preferably, steps (f) and (g) are repeated or carried out simultaneously for all unique barcode sequences. This allows the determination of the expression patterns of all first cells that were co-compartmentalized in a compartment with a polypeptide ligand expressed by a second cell or a cell-free expression system. In this case the method of the third aspect can also be described as a method for determining the effect of a ligand on the gene expression of a cell.

All other terms used with respect to the third aspect have the meanings as defined with respect to the first and second aspect of the invention. Further, all embodiments specified for the first aspect and second aspect that are applicable to the third aspect are also envisaged for the third aspect.

In a fourth aspect, the present invention relates to the use of the method of the third aspect to determine (i) the effect of antibodies on the gene expression of a target cell, wherein the antibodies were raised by immunizing a vertebrate with said target cell or one or more molecules or parts therefrom accessible on its surface, or (ii) the effect of polypeptide ligands on the gene expression of a target cell, wherein the polypeptide ligand is derived from a library.

The target cell is the first cell of the third aspect. In a preferred embodiment, the target cell is selected from the group consisting of a diseased cell, a stem cell, a pluripotent cell or a non-stem and non-pluripotent cell in which pluripotency is inducible by a polypeptide ligand. Preferably, the target cell is a human cell.

In alternative (i), the antibodies are preferably expressed by a cell of the B-cell lineage, more preferably by a plasma cell of the immunized vertebrate.

In a particular embodiment, the use according to alternative (i) does not comprise the immunization of the vertebrate itself or the isolation of cells from the vertebrate, but its in vitro application using the cells from the vertebrate after they have been isolated from the vertebrate.

All other terms used with respect to the fourth aspect have the meanings as defined with respect to the first, second and third aspect of the invention. Further, all embodiments specified for the first aspect, second and third aspect that are applicable to the fourth aspect are also envisaged for the fourth aspect.

The invention is described by way of the following examples which are to be construed as merely illustrative and not limitative of the scope of the invention.

EXAMPLES

Example 1: Selection of Antibodies with Anti-Inflammatory Properties, Using Known Drug Targets Methodology: Mice are immunized with epitopes of human cell-surface receptors involved in the regulation of inflammation pathways, such as Adenosine A1 receptor, CD7, CD43, CD45, integrins, CD2, CD3 (J. L. Cash, L. V. Norling and M. Perretti, Drug discovery today, 2014, 19, 1186-1192). Subsequent to one or more booster injections, B-cells are isolated from spleen and/or bone marrow. Then the B-cells are co-encapsulated into 660 pL droplets (J. Clausell-Tormos et al., Chem Biol, 2008, 15, 427-437), together with human cells showing a disease-associated inflammation genotype, e.g. cell models for arthritis or multiple sclerosis, showing a high expression of inflammation-associated mRNAs (C. Lambert et al., Arthritis Rheumatol, 2014, 66, 960-968; W. R. Swindell et al., Bmc Genomics, 2013, 14; A. K. Kemppinen et al., Bmj Open, 2011, 1). For encapsulation, a cell density much higher than in previous single-cell genomics studies (A. M. Klein et al., Cell, 2015, 161, 1187-1201; E. Z. Macosko et al., Cell, 2015, 161, 1202-1214) is chosen. Rather than using maximally $1 \times 10E5$ cells/mL, a cell density of $\sim 3 \times 10E6$/mL (for a 1:1 mixture of both cell types) is used. This is to achieve a high probability for the co-encapsulation of two cells into the same droplet, e.g. by using a $\lambda$-value (cell density multiplied by the droplet volume) of 2, rather than $\ll 1$ as for previous single-cell genomics studies (A. M. Klein et al., Cell, 2015, 161, 1187-1201; E. Z. Macosko et al., Cell, 2015, 161, 1202-1214). In addition to the two cell types, beads or gel particles providing polyT primers (or primers annealing with specifically targeted mRNA sequences) with unique sample barcodes and unique molecular identifiers (UMIs) are co-encapsulated into the 660 pL droplets. The resulting emulsion is then incubated at 37° C. for a time period sufficient to allow for an effect of the B-cell-secreted antibodies on the expression pattern of the human target cells (typically between a few hours up to 1 or 2 days). This is in contrast to previous studies (A. M. Klein et al., Cell, 2015, 161, 1187-1201; E. Z. Macosko et al., Cell, 2015, 161, 1202-1214), in which the incubation period was chosen as short as possible to avoid changes of the expression pattern while the cells are inside the microfluidic droplets. Following incubation, cell lysis is initiated by either fusing the cell-containing droplets with droplets hosting lysis buffer, or by storing the droplets in arrays (H. X. Hu et al., Lab on a Chip, 2015, 15, 3989-3993) and applying them to repeated freezing thawing cycles. Upon cell lysis, cellular mRNA of both cell types (murine B-cell and human target cell) is released within the droplets and thus hybridizes with the polyT primers on the beads or within the gel particles. In consequence, the mRNAs of both cell types hybridize with primers showing the same sample barcode. Subsequently, the emulsion is broken and all beads or gel particles are pooled and washed. Then, reverse transcription of the bound mRNA is carried out in bulk (using macroscopic test tubes). Alternatively, the cDNA synthesis can also be performed inside the droplets, prior to breaking the emulsion. All newly generated cDNA is ultimately amplified by PCR and applied to next generation sequencing using existing protocols, e.g. for the Illumina sequencing platforms (E. Z. Macosko et al., *Cell*, 2015, 161, 1202-1214; P. Brennecke et al., Nature methods, 2013, 10, 1093-1095).

Sequence analysis of the experiment is then carried out as follows: First of all, mRNA expression patterns of the target cells have to be distinguished from those of the B-cells. This can be done in two different ways: i) exploiting the limited sequence homology between the murine B-cell donor and the human target cell or ii) by subtracting a reference B-cell transcriptome. This is possible, as the expression pattern of different B-cells does not vary much, apart from the expression of unique clonal antibodies. In contrast, the expression pattern of the human target cells will vary depending on the B-cell-secreted antibody it was incubated with. As a second step of the sequence analysis, the expression pattern of individual human target cells, which can be discriminated based on the sample barcodes, is screened for anti-inflammatory mRNA expression patterns, e.g. downregulation of the further above defined inflammation-associated mRNAs. Once a cell with a corresponding transcriptome has been identified, all sequencing data is screened for antibody-encoding Vl and Vh genes with the same barcode, coming from the B-cell that was in the same droplet as the human target cell with the anti-inflammatory expression pattern.

This allows to identify antibodies with the desired anti-inflammatory effect on the target cells. A scheme of this approach is shown in FIG. 2.

Example 2: Selection of Anti-Cancer Antibodies, Acting on Potentially Unknown Drug Targets to Modulate Known Cancer-Relevant Pathways Methodology: Mice are immunized with human cancer cells or membrane extracts thereof. Subsequent to one or more booster injections, B-cells are isolated from spleen and/or bone marrow. Then the B-cells are co-encapsulated into 660 pL droplets J. Clausell-Tormos et al., *Chem Biol*, 2008, 15, 427-437), together with the cancer cells used for immunization. These can be human cell lines or primary cancer cells from tumors in which particular oncogenes (e.g. BRAF, KRAS) are overexpressed and/or mutated. For encapsulation, a cell density much higher than in previous single-cell genomics studies (A. M. Klein et al., Cell, 2015, 161, 1187-1201; E. Z. Macosko et al., Cell, 2015, 161, 1202-1214) is chosen. Rather than using maximally 1×10E5 cells/mL, a cell density of ~3×10E6/mL (for a 1:1 mixture of both cell types) is used. This is to achieve a high probability for the co-encapsulation of two cells into the same droplet, e.g. by using a λ-value (cell density multiplied by the droplet volume) of 2, rather than <<1 as for previous single-cell genomics studies (A. M. Klein et al., Cell, 2015, 161, 1187-1201; E. Z. Macosko et al., Cell, 2015, 161, 1202-1214). In addition to the two cell types, beads or gel particles providing polyT primers (or primers annealing with specifically targeted mRNA sequences) with unique sample barcodes and unique molecular identifiers (UMIs) are co-encapsulated into the 660 pL droplets. The resulting emulsion is then incubated at 37° C. for a time period sufficient to allow for an effect of the B-cell-secreted antibodies on the expression pattern of the human target cells (typically between a few hours up to 1 or 2 days). This is in contrast to previous studies (A. M. Klein et al., Cell, 2015, 161, 1187-1201; E. Z. Macosko et al., Cell, 2015, 161, 1202-1214), in which the incubation period was chosen as short as possible to avoid changes of the expression pattern while the cells are inside the microfluidic droplets. Following incubation, cell lysis is initiated by either fusing the cell-containing droplets with droplets hosting lysis buffer, or by storing the droplets in arrays (H. X. Hu et al., *Lab on a Chip*, 2015, 15, 3989-3993) and applying them to repeated freezing thawing cycles. Upon cell lysis, cellular mRNA of both cell types (murine B-cell and human target cell) is released within the droplets and thus hybridizes with the polyT primers on the beads or within the gel particles. In consequence, the mRNAs of both cell types hybridize with primers showing the same sample barcode. Subsequently, the emulsion is broken and all beads or gel particles are pooled and washed. Then, reverse transcription of the bound mRNA is carried out in bulk, e.g. using macroscopic test tubes. Alternatively, the cDNA synthesis can also be performed inside the droplets, prior to breaking the emulsion. All newly generated cDNA is ultimately amplified by PCR and applied to next generation sequencing using existing protocols, e.g. for the Illumina sequencing platforms (E. Z. Macosko et al., *Cell*, 2015, 161, 1202-1214; P. Brennecke et al., Nature methods, 2013, 10, 1093-1095).

Sequence analysis of the experiment is then carried out as follows: First of all, mRNA expression patterns of the target cells have to be distinguished from those of the B-cells. This can be done in two different ways: i) exploiting the limited sequence homology between the murine B-cell donor and the human target cell or ii) by subtracting a reference B-cell transcriptome. This is possible as the expression pattern of different B-cells does not vary much, apart from the expression of unique clonal antibodies. In contrast, the expression pattern of the human target cells will vary depending on the B-cell-secreted antibody it was incubated with. As a second step of the sequence analysis, the expression pattern of individual human target cells, which can be discriminated based on the sample barcodes, is screened for downregulation of particular oncogenes, e.g. reduced abundance of mRNAs encoding oncogenes. Once a cell with a corresponding transcriptome has been identified, all sequencing data is screened for antibody-encoding Vl and Vh genes with the same barcode, coming from the B-cell that was in the same droplet as the human cancer cell. This allows to identify antibodies with the desired therapeutic effect on the human cancer cells. A scheme of this approach is shown in FIG. 2.

Example 3: Selection of Antibodies Shifting a Disease Associated Global Expression Profile Towards its Healthy Counterpart Methodology: Mice are immunized with human cancer cells or membrane extracts thereof. Subsequent to some booster injections, B-cells are isolated from spleen and/or bone marrow. Then the B-cells are co-encapsulated into 660 pL droplets (J. Clausell-Tormos et al., *Chem Biol*, 2008, 15, 427-437) together with the cancer cells used for immunization. For encapsulation, a cell density much higher than in previous single-cell genomics studies (A. M. Klein et al., Cell, 2015, 161, 1187-1201; E. Z. Macosko et al., Cell, 2015, 161, 1202-1214) is chosen. Rather than using maximally 1×10E5 cells/mL, a cell density of ~3×10E6/mL (for a 1:1 mixture of both cell types) is used. This is to achieve a high probability for the co-encapsulation of two cells into the same droplet, e.g. by using a λ-value (cell density multiplied by the droplet volume) of 2, rather than <<1 as for previous single-cell genomics studies (A. M. Klein et al., Cell, 2015, 161, 1187-1201; E. Z. Macosko et al., Cell, 2015, 161, 1202-1214). In addition to the two cell types, beads or gel particles providing polyT primers (or primers annealing with specifically targeted mRNA sequences) with unique sample barcodes and unique molecular identifiers (UMIs) are co-encapsulated into the 660 pL droplets. The resulting emulsion is then incubated at 37° C. for a time period sufficient to allow for an effect of the B-cell-secreted antibodies on the expression pattern of the human target cells (typically between a few hours up to 1 or 2 days). This is in contrast to previous studies (A. M. Klein et al., Cell, 2015, 161, 1187-1201; E. Z. Macosko et al., Cell, 2015, 161, 1202-1214), in which the incubation period was chosen as short as possible to avoid changes of the expression pattern while the cells are inside the microfluidic droplets. Following incubation, cell lysis is initiated by either fusing the cell-containing droplets with droplets hosting lysis buffer, or by storing the droplets in arrays (H. X. Hu et al., Lab on a Chip, 2015, 15, 3989-3993) and applying them to repeated freezing thawing cycles. Upon cell lysis, cellular mRNA of both cell types (murine B-cell and human target cell) is released within the droplets and thus hybridizes with the polyT primers on the beads or within the gel particles. In consequence, the mRNAs of both cell types hybridize with primers showing the same sample barcode. Subsequently, the emulsion is broken and all beads or gel particles are pooled and washed. Then, reverse transcription of the bound mRNA is carried out in bulk, e.g. using macroscopic test tubes. Alternatively, the cDNA synthesis can also be performed inside the droplets, prior to breaking the emulsion. All newly generated cDNA is ultimately amplified by PCR and applied to next generation sequencing using existing protocols, e.g. for the Illumina sequencing platforms (E. Z. Macosko et al., Cell, 2015, 161, 1202-1214; P. Brennecke et al., Nature methods, 2013, 10, 1093-1095).

Sequence analysis of the experiment is then carried out as follows: First of all, mRNA expression patterns of the target cells have to be distinguished from those of the B-cells. This can be done in two different ways: i) exploiting the limited sequence homology between the murine B-cell donor and the human target cell or ii) by subtracting a reference B-cell transcriptome. This is possible, as the expression pattern of different B-cells does not vary much, apart from the expression of unique clonal antibodies. In contrast, the expression pattern of the human target cells will vary depending on the B-cell-secreted antibody it was incubated with. As a second step of the sequence analysis, the expression pattern of individual human cancer cells, which can be discriminated based on the sample barcodes, is screened for a change of the global expression pattern towards their healthy counterpart. For example, when encapsulating pancreatic tumor cells as a target, one can take the global expression pattern of healthy pancreatic cells and look for pancreatic tumor cells which, in presence of a particular antibody, show less difference to their healthy counterpart, e.g. normal or even higher expression levels of pro-apoptotic factors, lower expression levels of oncogenes, etc. Once a cell with a corresponding transcriptome has been identified, all sequencing data is screened for antibody-encoding Vl and Vh genes with the same barcode, coming from the B-cell that was in the same droplet as the human cancer cell. This allows to identify antibodies with the desired therapeutic effect on the human cancer cells.

Example 4: Distinguishing Between Sequences from Different Species 96 samples comprising:
a) A single murine hybridoma cell secreting α-Her2 antibodies and a bead displaying uniquely barcoded poly-T primers (32 samples)
b) A single human SKBR3 cancer cell and a bead displaying uniquely barcoded poly-T primers (32 samples)
c) A single murine α-Her2 hybridoma cell, a single human cancer cell (pre-incubated with α-Her2 antibodies) and a bead displaying uniquely barcoded poly-T primers (32 samples) were set up manually in PCR tubes using a total volume of 4 µl. Cells were lysed and the cellular mRNA of the cells (human and murine in case of sample c) was hybridized to the beads (obtained commercially from Chemgenes). Subsequently the samples were pooled and RT was carried out using Maxima H Minus Reverse Transcriptase (Thermo Fisher). Second strand synthesis was performed using a template switch oligonucleotide (sequence). Then a next generation sequencing library was prepared based on the DropSeq protocol (http://mccarrolllab.com/dropseq/). Finally the samples were sequenced on an Illumina platform and the data was analyzed. This entire workflow is illustrated in FIG. 3 (sample setup) and FIG. 4 (subsequent steps).

After grouping all sequences according to the different barcodes, the number of human and murine reads was plotted in an XY diagram (FIG. 5). As expected, three different populations with approximately equal occurrence were observed: Samples showing sequences that could be assigned almost exclusively to the murine genome (corresponding to sample composition a; labeled "mm" in FIG. 5), samples showing sequences that could be assigned almost exclusively to the human genome (corresponding to sample composition b; labeled "hs" in FIG. 5) and samples showing sequences that could be assigned at approximately equal fractions to the murine and human genome (corresponding to sample composition a; labeled "mm-hs" in FIG. 5).

Based on a strict quality threshold, some samples were not automatically assigned to any given population (e.g. samples for which the number of reads was below a threshold of 300 reads or samples showing sequences matching both, the murine and human genome, but not in approximately equal fractions). These are shown black in FIG. 5. Note however, that the number of these non-assigned samples can be decreased by lowering the threshold or by increasing the total number of reads per sample (preferred).

More importantly, for all samples that could be assigned to sample composition c (containing a single murine hybridoma cell and a human cancer cell; as desired for the current invention) murine antibody-encoding sequences as well as human mRNA sequences were obtained. Taken together, this clearly shows that the approach can be used to analyze the transcriptome of a target cell (e.g. to infer cellular states, modulated signalling pathways) in response to incubation with a particular antibody, and simultaneously provide the identity of that antibody.

Example 5: Generating Microfluidic Droplets Comprising a First Cell, One Second Cell and a Set of Barcode Oligonucleotides To show the principle of the generation of a plurality of compartments according to the invention, beads were used instead of the cells and the set of barcode oligonucleotides. More specifically, the three following particles were used as a model system:
1.) Green fluorescent beads (Bangslabs, Catalog Nr. FS07F) mimicking antibody-expressing cells,
2.) Blue fluorescent beads (Thermo Fisher, Catalog Nr. F8829) mimicking target cells,
3.) Non-fluorescent beads (Tosoh Bioscience, Catalog Nr. 19815), mimicking beads with barcoded primers.

To obtain a high fraction of droplets hosting all three particles, two particular measures clearly distinguishing the current invention from previous approaches were chosen:
a) the used particle densities were much higher as compared to prior art. A 1:1 mix of green and blue fluorescent beads was adjusted to a total density of 2.5 million per milliliter. Using a microfluidic chip with the same geometry as described in the Macosco et al., Cell 2015 publication, droplets with a volume of approximately 250 pL were generated while co-injecting the non-fluorescent beads (adjusted to a density of 1.5e5/ ml). More than 50% of these droplets contained at least one fluorescent particle (mimicking a cell) straight from the start.
b) the resulting emulsion was sorted for double positive blue-green droplets (indicating the presence of both cell types; as described in Hu, Eustace and Merten, Lab Chip 2015).

Subsequent microscopic analysis of the droplets revealed the following occupancies:

TABLE 1

| Occupancy | Number of droplets | % |
|---|---|---|
| Bc Beads = 0<br>Green beads ≥ 1<br>Blue beads ≥ 1 | 74 | 87.05 |
| Bc Beads ≥ 1<br>Green beads ≥ 1<br>Blue beads ≥ 1 | 10 | 11.76 |
| Bc Beads = 1<br>Green beads = 1<br>Blue beads ≥ 1 | 6 | 7.06 |
| Bc Beads = 1<br>Green beads = 1<br>Blue beads = 1 | 5 | 5.88 |
| empty | 1 | 1.12 |
| total | 85 | 100 |

Taken together, these results clearly indicate that emulsions in which the fraction of droplets hosting three different particles (e.g. two different types of cells and beads for the barcoding of cellular mRNA) exceeds 10% can be easily generated by taking measures such as high cell densities and subsequent multi-colour sorting steps. Emulsions in which the fraction of droplets hosting three different particles, of which two are single particles (e.g. a single bead for the barcoding of cellular mRNA, a first cell and a single second cell) exceeds 5% being 7.06% in this particular example. Even when only looking at droplets hosting exactly one object of each type, an overall fraction exceeding 5% can be easily obtained. These numbers can be improved by optimizing parameters such as cell and bead densities, sorting chips and sorting software, etc., which is within the average skill in the art.

Noteworthy, the sorting step is a powerful tool in this approach but not an essential requirement: Based on Poisson statistics one can obtain droplets hosting exactly one of three different particles at a maximum frequency of 5% when adjusting the density of each particle to 1 per droplet volume. Furthermore, deterministic cell encapsulation devices have been described whose efficiency exceeds the limits based by Poisson statistics (e.g. Kemna E W, Schoeman R M, Wolbers F, Vermes I, Weitz D A, van den Berg A. Lab Chip. 12(16):2881-7, 2012. doi: 10.1039/c21c00013j). Hence, there are a variety of different ways for achieving a high fraction of droplets hosting three different particles. Particularly helpful for achieving this is to use particularly high particle densities, at least 4-10 times higher as compared to existing single cell transcriptomics approaches, or to perform subsequent sorting steps for droplets with the desired occupancy.

The invention claimed is:

1. A plurality of microfluidic compartments, wherein at least 1% of said compartments form a subset in which each compartment is a droplet comprising:
    (i) a first cell,
    (ii) one second cell, the second cell expressing a polypeptide ligand intended to specifically bind to a molecule or part thereof accessible on a surface of the first cell, wherein the one second cell is a cell of B-cell lineage and
    (iii) a set of barcode oligonucleotides each comprising a barcode sequence unique to the set and a sequence capable of binding specifically to mRNA and/or cDNA of the first cell and mRNA and/or cDNA of the one second cell.

2. The plurality of microfluidic compartments of claim 1, wherein the subset is at least 5% of the plurality of microfluidic compartments.

3. The plurality of microfluidic compartments of claim 1, wherein the first cell and the second cell are derived from different species.

4. The plurality of microfluidic compartments of claim 1, wherein the molecule or part thereof accessible on the surface of the first cell is a cell signaling receptor.

5. The plurality of microfluidic compartments of claim 1, wherein the first cell is a diseased cell, a stem or pluripotent cell, or a cell in which pluripotency is inducible by a polypeptide ligand.

6. The plurality of microfluidic compartments of claim 1, wherein the second cell is a non-human plasma cell of the B-cell lineage and the polypeptide ligand is an antibody produced by the plasma cell.

7. The plurality of microfluidic compartments of claim 1, wherein the polypeptide ligand is selected from the group consisting of an antibody, an antibody derivative and an antibody mimetic.

8. The plurality of microfluidic compartments of claim 1, wherein the set of barcode oligonucleotides is linked to a bead.

9. The plurality of microfluidic compartments of claim 1, wherein said sequence capable of binding specifically to mRNA and/or cDNA is a sequence capable of binding specifically to an mRNA 3' poly(A) tail or to a gene-specific sequence.

10. The plurality of microfluidic compartments of claim 1, the compartments of said subset of the plurality of compartments each further comprising one or more of the following:
    a cell lytic agent,
    an RNase-inhibitor,
    a DNase,
    reagents for a reverse transcription reaction, and/or
    a drug or drug candidate for treating the diseased cell or the disease the diseased cell is derived from, wherein the diseased cell it the first cell.

11. A method for generating a plurality of microfluidic compartments according to claim 1, comprising the steps of:
    (a) introducing into a microfluidic system: (i) a fluid comprising a plurality of first cells, (ii) a fluid comprising a plurality of second cells each expressing a polypeptide ligand which is intended to specifically bind to a molecule or part thereof accessible on the surface of a first cell, and (iii) a fluid comprising sets of barcode oligonucleotides, wherein the barcode oligonucleotides of each set comprises a barcode sequence unique to the set, and a sequence capable of binding specifically to mRNA and/or cDNA of the first cell and mRNA and/or cDNA of the one second cell, and
    (b) repeatedly co-compartmentalizing one of the first cells, one of the second cells, and a set of the barcode oligonucleotides into microfluidic compartments, such that the size of the subset of compartments in the plurality of compartments is at least 1%.

12. A method for determining the gene expression of a cell, comprising the steps:
    (a) providing a plurality of microfluidic compartments wherein at least 1% of said compartments form a subset in which each compartment is a droplet comprising:
        (i) a first cell,
        (ii) one second cell or one cell-free expression system, the second cell or the cell-free expression system expressing a polypeptide ligand intended to specifically bind to a molecule or part thereof accessible on a surface of the first cell, and (iii) a set of barcode oligonucleotides each comprising a barcode sequence unique to the set and a sequence capable of binding specifically to mRNA and/or cDNA of the first cell and mRNA and/or cDNA of the one second cell or the one cell-free expression system, (b) lysing the cells comprised in the compartments, (c) reverse transcribing mRNA released from the cells to cDNA, (d) amplifying the cDNA, (e) determining the sequence and optionally the respective amount of the cDNA, and (f) selecting sequences comprising the same barcode sequence, wherein the following sequences are excluded:

sequences derived from a second cell or a cell-free expression system, sequences comprising a unique barcode sequence that is not associated in other sequences with a nucleotide sequence encoding for a polypeptide ligand expressed by a second cell or a cell-free expression system, sequences comprising a unique barcode sequence that is associated with a nucleotide sequence encoding for more than one polypeptide ligand expressed by a second cell or a cell-free expression system, wherein step (c) or step (d) is carried out with a barcode oligonucleotide as a primer.

13. The method of claim 12, wherein the barcode oligonucleotide has a poly(dT) or poly(dU) sequence if it is used as a primer in step (c) or wherein the barcode oligonucleotide is part of a gene-specific primer pair if it is used as a primer in step (d).

14. The method of claim 12, wherein the contents of the compartments are pooled after annealing of the barcode oligonucleotide primer and at any stage prior to step (e).

15. The method of claim 12 wherein the method is for determining at least one of: (i) the effect of antibodies on the gene expression of a target cell, wherein the antibodies were raised by immunizing a vertebrate with said target cell or one or more molecules or parts therefrom accessible on its surface, or (ii) the effect of polypeptide ligands on the gene expression of a target cell, wherein the polypeptide ligand is derived from a library.

16. The plurality of microfluidic compartments of claim 1, wherein the sequence capable of binding specifically to mRNA and/or cDNA is at a 3' end of the barcode oligonucleotide, and the sequence capable of binding specifically to mRNA and/or cDNA is capable of priming a DNA polymerization.

17. A plurality of microfluidic compartments, wherein at least 1% of said compartments form a subset in which each compartment is a droplet comprising:

(i) a first cell, (ii) one second cell or one cell-free expression system, the second cell or the cell-free expression system expressing a polypeptide ligand intended to specifically bind to a molecule or part thereof accessible on a surface of the first cell, and (iii) a set of barcode oligonucleotides each comprising a barcode sequence unique to the set and a sequence capable of binding specifically to mRNA and/or cDNA of the first cell and/or of the one second cell or the one cell-free expression system, wherein the compartment volume of the subset and the cell concentration of the first cell (i), the cell concentration or cell-free expression system concentration of the one second cell or the one cell-free expression system (ii), and the set concentration of the set of barcode oligonucleotides (iii) is such that $\lambda$ is between 0.1 and 2 for each of the cell concentration of the first cell (i), the cell concentration of the one second cell or cell-free expression system concentration of the one cell-free expression system (ii), and the set concentration of the set of barcode oligonucleotides (iii), wherein $\lambda$ is the average number of cells, cell-free expressions systems and sets of the barcode oligonucleotides per compartment volume of the subset.

18. The plurality of microfluidic compartments of claim 17, wherein the total density of the first cell and the one second cell or the one cell-free expression system in the subset of said compartments is 0.5 to $10 \times 10^6$ cells per milliliter.

19. A method for generating the plurality of microfluidic compartments of claim 17, comprising the steps of:

(a) introducing into a microfluidic system: (i) a fluid comprising a plurality of first cells, (ii) a fluid comprising a plurality of second cells or cell-free expression systems each expressing a polypeptide ligand which is intended to specifically bind to a molecule or part thereof accessible on the surface of a first cell, and (iii) a fluid comprising sets of barcode oligonucleotides, wherein the barcode oligonucleotides of each set comprises a barcode sequence unique to the set, and a sequence capable of binding specifically to mRNA and/or cDNA of the first cell and mRNA and/or cDNA of the one second cell or the one cell-free expression system, and (b) repeatedly co-compartmentalizing one of the first cells, one of the second cells or one of the cell-free expression systems, and a set of the barcode oligonucleotides into microfluidic compartments, such that the size of the subset of compartments in the plurality of compartments is at least 1%.

20. A method for determining the gene expression of a cell, comprising the steps:

(a) providing the plurality of microfluidic compartments according to claim 17, (b) lysing the cells comprised in the compartments, (c) reverse transcribing mRNA released from the cells to cDNA, (d) amplifying the cDNA, (e) determining the sequence and optionally the respective amount of the cDNA, and (f) selecting sequences comprising the same barcode sequence, wherein the following sequences are excluded:

sequences derived from a second cell or a cell-free expression system, sequences comprising a unique barcode sequence that is not associated in other sequences with a nucleotide sequence encoding for a polypeptide ligand expressed by a second cell or a cell-free expression system, sequences comprising a unique barcode sequence that is associated with a nucleotide sequence encoding for more than one polypeptide ligand expressed by a second cell or a cell-free expression system, wherein step (c) or step (d) is carried out with a barcode oligonucleotide as a primer.

21. The method of claim 20, wherein the barcode oligonucleotide has a poly(dT) or poly(dU) sequence if it is used as a primer in step (c) or wherein the barcode oligonucleotide is part of a gene-specific primer pair if it is used as a primer in step (d).

22. The method of claim 20, wherein the contents of the compartments are pooled after annealing of the barcode oligonucleotide primer and at any stage prior to step (e).

23. The method of claim 20, wherein the method is for determining (i) the effect of antibodies on the gene expression of a target cell, wherein the antibodies were raised by immunizing a vertebrate with said target cell or one or more molecules or parts therefrom accessible on its surface, or (ii) the effect of polypeptide ligands on the gene expression of a target cell, wherein the polypeptide ligand is derived from a library.

24. The plurality of microfluidic compartments of claim 1, wherein the droplet includes an aqueous liquid in an immiscible liquid.

25. The method of claim 12, wherein the droplet includes an aqueous liquid in an immiscible liquid.

26. The plurality of microfluidic compartments of claim 17, wherein the droplet includes an aqueous liquid in an immiscible liquid.

* * * * *